(12) United States Patent
Grau-Campistany et al.

(10) Patent No.: US 11,246,818 B2
(45) Date of Patent: Feb. 15, 2022

(54) PEPTIDES AND COMPOSITIONS FOR USE IN COSMETICS

(71) Applicant: LIPOTRUE, S.L., Gava (ES)

(72) Inventors: Ariadna Grau-Campistany, Barcelona (ES); Silvia Pastor, Alicante (ES); Patricia Carulla, Barcelona (ES); Juan Carlos Escudero, Barcelona (ES)

(73) Assignee: LIPOTRUE, S.L., Gava (ES)

( * ) Notice: Subject to any disclaimer, the term of this patent is extended or adjusted under 35 U.S.C. 154(b) by 109 days.

(21) Appl. No.: 16/485,310

(22) PCT Filed: Feb. 23, 2018

(86) PCT No.: PCT/EP2018/054587
§ 371 (c)(1),
(2) Date: Aug. 12, 2019

(87) PCT Pub. No.: WO2018/154080
PCT Pub. Date: Aug. 30, 2018

(65) Prior Publication Data
US 2019/0388325 A1    Dec. 26, 2019

(30) Foreign Application Priority Data
Feb. 24, 2017 (EP) .................................. 17382092

(51) Int. Cl.
| | |
|---|---|
| *C07K 5/10* | (2006.01) |
| *C07K 7/00* | (2006.01) |
| *A61K 8/64* | (2006.01) |
| *A61K 8/06* | (2006.01) |
| *A61Q 19/02* | (2006.01) |
| *A61Q 19/08* | (2006.01) |
| *C07K 5/00* | (2006.01) |
| *C07K 7/06* | (2006.01) |

(52) U.S. Cl.
CPC ................ *A61K 8/64* (2013.01); *A61K 8/06* (2013.01); *A61Q 19/02* (2013.01); *A61Q 19/08* (2013.01); *C07K 5/00* (2013.01); *C07K 7/06* (2013.01)

(58) Field of Classification Search
None
See application file for complete search history.

(56) References Cited

U.S. PATENT DOCUMENTS

| | | | | |
|---|---|---|---|---|
| 2006/0217891 | A1* | 9/2006 | Tanuma | G16B 15/00 |
| | | | | 702/19 |
| 2008/0071706 | A1* | 3/2008 | Honda | G06N 3/0436 |
| | | | | 706/2 |
| 2009/0149339 | A1* | 6/2009 | Lu | C07K 14/705 |
| | | | | 506/9 |
| 2011/0305735 | A1 | 12/2011 | Cebrian et al. | |
| 2012/0135918 | A1* | 5/2012 | Bowers | A61K 38/25 |
| | | | | 514/4.8 |
| 2012/0219505 | A1* | 8/2012 | Wang | G01N 33/57419 |
| | | | | 424/9.2 |
| 2014/0044796 | A1* | 2/2014 | Kehrel | G01N 33/6893 |
| | | | | 424/530 |

FOREIGN PATENT DOCUMENTS

| | | | | |
|---|---|---|---|---|
| EP | 2649983 A1 | 10/2013 | | |
| WO | WO 2004/099784 | * 11/2004 | ............. | C07K 16/18 |
| WO | WO 2017/096076 | * 6/2017 | ............. | C08F 293/00 |

OTHER PUBLICATIONS

Ballin, J. D., et al. Biochem. (2010), 49(9); 2018-2030 (Year: 2010).*
Technical Information bulletin from Thermo Electron Corp. 2004; 2 pgs. (Year: 2004).*
International Search Report and Written Opinion for Corresponding International Application No. PCT/EP2018/054587 (dated May 15, 2018) (14 Pages).

* cited by examiner

*Primary Examiner* — Kevin S Orwig
(74) *Attorney, Agent, or Firm* — Lucas & Mercanti, LLP

(57) ABSTRACT

A family of peptides with antioxidant and brightening activities is disclosed as well as cosmetic compositions having the peptides and cosmetic uses and methods of the peptides or cosmetic compositions.

9 Claims, 15 Drawing Sheets
Specification includes a Sequence Listing.

PEPTIDES AND COMPOSITIONS FOR USE IN COSMETICS

CROSS-REFERENCE TO RELATED APPLICATIONS

This Application is a 371 of PCT/EP2018/054587, filed Feb. 23, 2018, which claims the benefit of European Patent Application No. 17382092.9, filed Feb. 24, 2017, each of which are incorporated herein by reference.

FIELD OF THE INVENTION

The present invention relates to the field of cosmetics, more precisely to peptides and compositions with antioxidant and/or brightening activities and methods and uses thereof in the field of cosmetics.

BACKGROUND OF THE INVENTION

In the recent years, there has been a growing interest in the population to prevent, reduce or eliminate skin imperfections and damage caused by endogenous and environmental stressors, in order to maintain the skin with a healthy and youthful appearance. This has led to an increasing interest in the reasons that lead to the appearance of skin imperfections and in the search of compounds and compositions which can prevent or alleviate skin imperfections.

Oxidation and oxidative stress are probably the most harmful contributors to skin aging and skin damaging, leading to degradation of the skin extracellular matrix (ECM) and to inflammatory processes among others (Bickers, D. R. Athar, M., *Oxidative Stress in the Pathogenesis of Skin Disease*, J. Inv. Dermatology, 2006; 126: 2565-2575). The origin of oxidation and oxidative stress is varied and can be induced by, for example, intrinsic factors, as a consequence of physiological ageing and more importantly by environmental factors such as pollution, smoking, photoaging (due to the effect of UV radiation) or other environmental factors that clearly contribute to ageing (Farage, M. A., Miller, K. W., Elsner, P., Maibach, H. I., *Intrinsic and extrinsic factors in skin ageing: a review*. Int J Cosmet Sci, 2008; 30: 87-95). Oxidation as a consequence of external factors (for example, pollution—ozone loss, greenhouse gases levels being higher than ever and particulate matter from anthropogenic sources becoming more frequently related to damaging health effects—) is, nowadays, one of the main accelerators of skin aging and the appearance of skin imperfections.

Oxidation and oxidative stress, among other consequences, generates oxygen-derived radicals and inflammation which, in turn produces, for example:

Peroxidation of cellular and subcellular polyunsaturated fatty acids (hereinafter, PUFAs) of lipid bilayers, which can lead to a decreased fluidity, loss of function and even cell death. Malondialdehyde (hereinafter, MDA) is one of the main lipid hydroperoxide-derived bifunctional electrophile from lipid peroxidation which binds covalently to deoxyribonucleic acid (hereinafter, DNA) generating adducts seriously damaging cellular metabolism and integrity.

Glycation, which is a non-enzymatic reaction between reducing sugars and proteins, lipids or nucleic acids which is accelerated due to the aforementioned factors. Schiff bases and Amadori products derived from the reaction between sugars and free amino groups can react irreversibly with other residues of peptides or proteins forming protein adducts or crosslinks or undergo further oxidative reactions yielding Advanced Glycation End products.

Other DNA damage. As already stated above, DNA is highly susceptible to oxidation. Both the sugar phosphate backbone and the nucleobases are direct targets for oxidizing agents. Guanin (G) is especially sensitive to oxidation by a variety of oxidants including hydroxyl radical (—OH), singlet oxygen ($^1O_2$) and derivatives of peroxynitrite (ONOO—). A common oxidized form of G is 8-oxoG and has been involved in genotoxic and mutagenic lesions.

Hyperpigmentation: Pigmentation can be due to multiple factors associated to an increase in oxidative stress such as UV radiation, inflammation, hormonal changes, lifestyle and environmental pollutants. In the latter case, aryl hydrocarbon receptor (hereinafter, AhR) is of special interest as it has been described that it plays a role in pigment formation by regulating the expression of genes coding for enzymes of the melanogenic pathway (Jux, B., Kadow, S., Luecke, S., Rannug, A., Krutmann, J. and Esser, C., *The Aryl Hydrocarbon Receptor Mediates UVB Radiation-Induced Skin Tanning*, J. of Inv. Dermatology, 131 (2011) 203-210), consequently, its activation by pollutants, such as those contained in tobacco smoke, causes hyperpigmentation (Nakamura, M., Ueda, Y., Hayashi, M., Kato, H., Furuhashi, T. and Morita, A., *Tobacco smoke-induced skin pigmentation is mediated by the aryl hydrocarbon receptor*, Experimental Dermatology, 22 (2013) 554-563).

Multiple strategies and compounds have been developed in order to fight against these undesirable ageing processes, such as topical antioxidants, such as, vitamins, retinoids, flavonoids, contained in plant extracts, or anti-inflammatory actives (Pillai, S., Oresajo, C., Hayward, J. *Ultraviolet radiation and skin ageing: roles of reactive oxygen spices, inflammation and protease activation, and strategies for prevention of inflammation induced matrix degradation—a review*, Int J Cosmet Sci, 2005; 27:17-34). However, some of these compounds are just able to act on one of these extrinsic factors, or are not compatible with sun exposure, making it necessary to use multiple products in order to obtain a complete effect on the skin.

The idea behind using antioxidants for skin-lightening activities lies in the hypothesis that the oxidative effect of UV-irradiation contributes to activation of melanogenesis. UV irradiation can produce reactive oxygen species (ROS) in the skin that can induce melanogenesis by activating tyrosinase. Redox agents can also influence skin pigmentation by interacting with copper at the active site of tyrosinase or with o-quinones to impede the oxidative polymerization of melanin intermediates. Antioxidants can also reduce the direct photooxidation of pre-existing melanin.

Besides this antioxidant mechanism, there are several other strategies to reduce the level of pigmentation in the skin. Many of the existing brightening active ingredients have a tyrosinase-inhibiting effect on the melanocyte leading to reduced total melanin production (for example, kojic acid or arbutin). Others have an effect on the transfer of melanin from melanocytes to keratinocytes (for example, nicotinamide and soyabean) or increase the desquamation of the skin to remove excessive melanin content (Gillbro J M, Olsson M J. *The melanogenesis and mechanisms of skin-lightening agents—existing and new approaches*. Int J Cosmet Sci. 2011 June; 33(3):210-21). Paracrine communication between human fibroblasts or keratinocytes and melanocytes also contributes to cutaneous pigmentation (Imokawa G, Yada Y, Morisaki N, Kimura *Biological characterization of human fibroblast-derived mitogenic factors for human melanocytes*. M. Biochem J. 1998 Mar. 15; 330 (Pt 3):1235-9; Hirobe T, *Keratinocytes regulate the function of melanocytes*, Dermatologica Sinica, 2014; 32(4)). Thus, modulation of soluble factors (for example, hepatocyte growth factor (HGF), stem cell factor (SCF, also known as KIT-ligand), Proopiomelanocortin (POMC), Endothelin (EDN1), nerve growth factor (NGF) and Dickkopf-related protein 1 (DKK1 or TP53) is also a target in the study of skin-lightening agents.

Hence, it is desirable to find substances or active ingredients with a wide-spectrum antioxidant and/or brightening activities which can be applied in the field of cosmetics to prevent or treat skin imperfections appearing as the result of environmental oxidative stress (for example, pollution and UV radiation), to correct undesirable pigmentation of the skin and/or to prevent or treat aging or photo-aging skin imperfections.

SUMMARY OF THE INVENTION

The inventors of the present patent, after extensive and exhaustive research, have surprisingly found a family of peptides with wide-spectrum antioxidant and/or brightening activity, and, hence, peptides that solve the above-mentioned problems and needs present in the state of the art.

DETAILED DESCRIPTION OF THE INVENTION

Figure 1A:
FIG. 1A shows the trolox equivalents obtained for the treatment with Ac-SEQ ID NO: 1-NH$_2$.
Figure 1B:
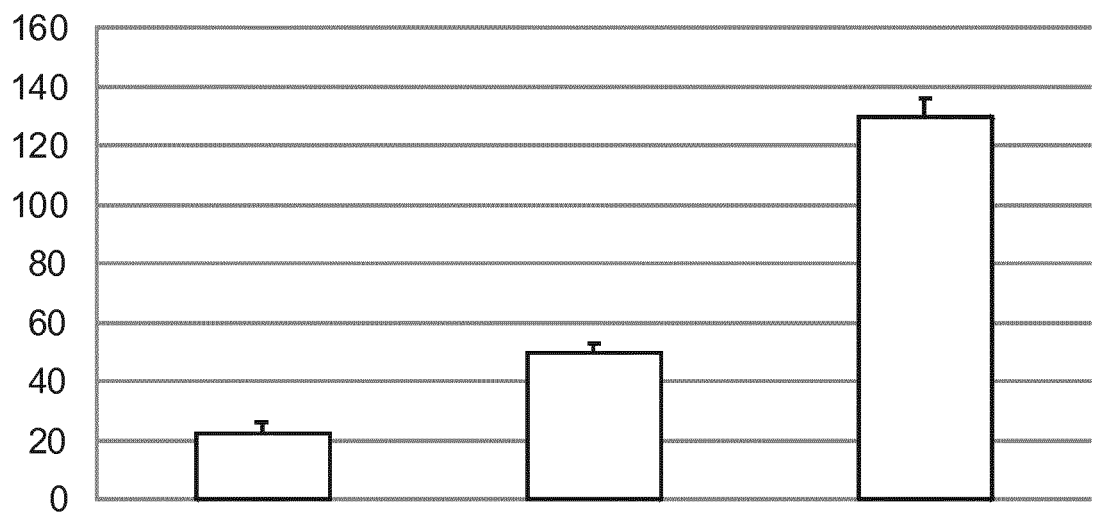
FIG. 1B shows the trolox equivalents obtained for the treatment with Ac-SEQ ID NO: 2-NH$_2$.
Figure 1C:
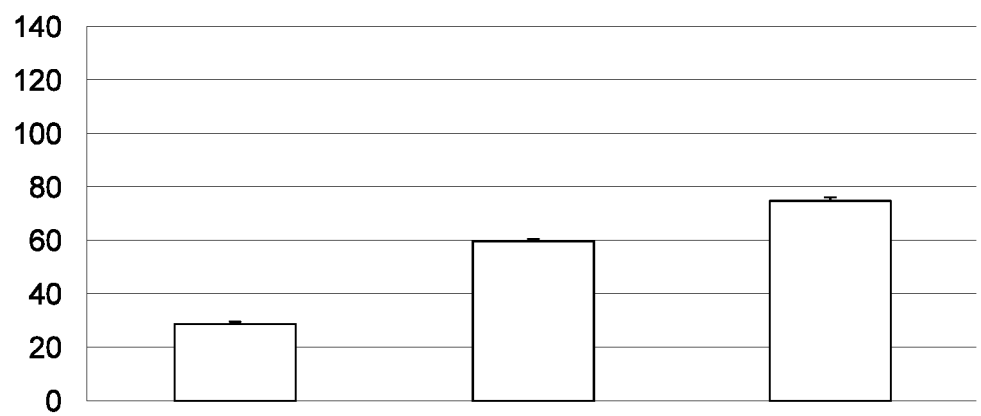
FIG. 1C shows the trolox equivalents obtained for the treatment with Ac-SEQ ID NO: 3-NH$_2$.
Figure 1D:
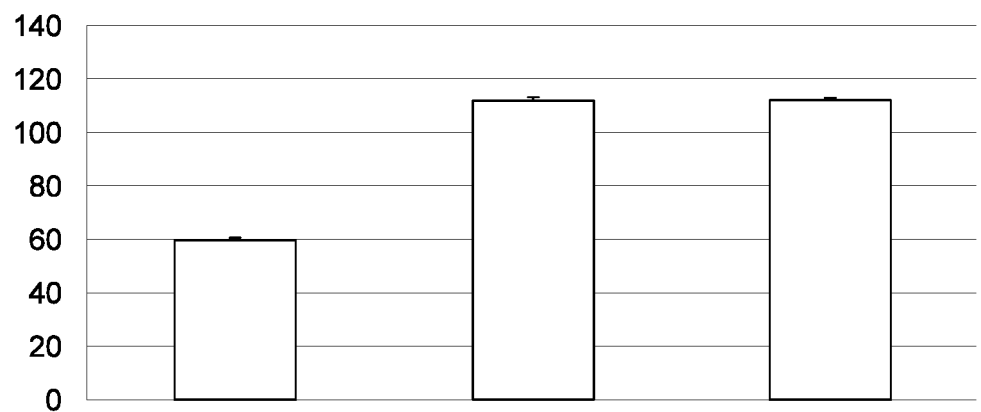
FIG. 1D shows the trolox equivalents obtained for the treatment with Ferulic acid-SEQ ID NO: 2-NH$_2$.
Figure 1E:
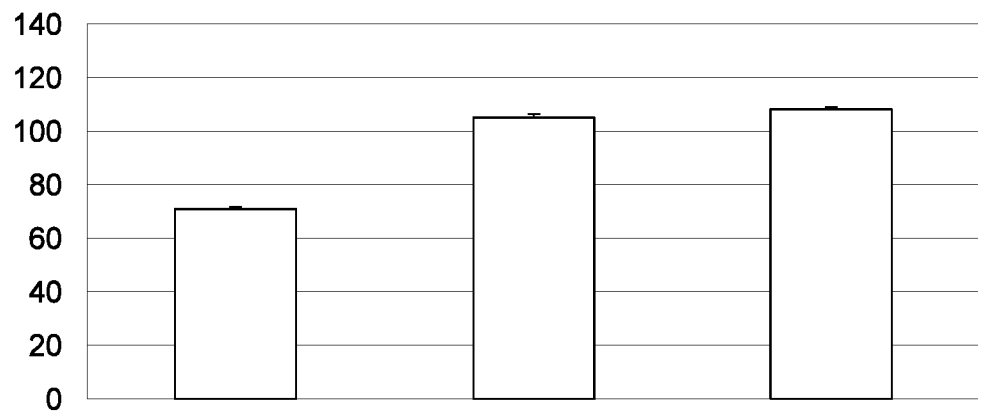
FIG. 1E shows the trolox equivalents obtained for the treatment with AA-2G.
Figure 1F:
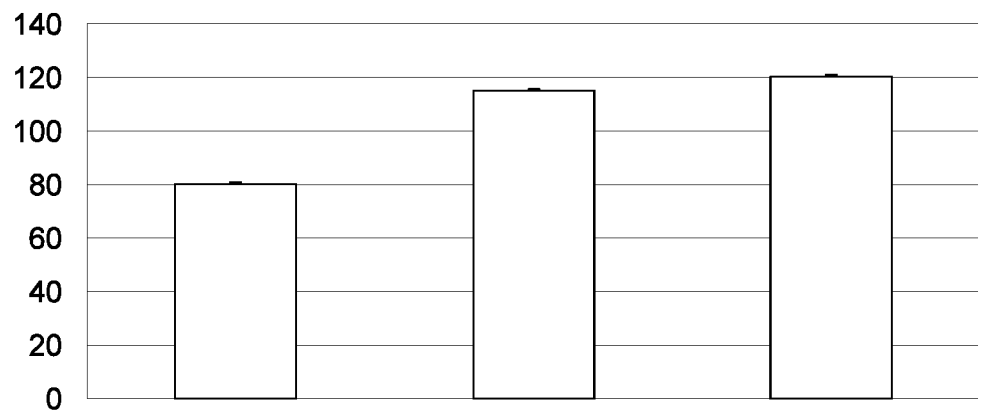
FIG. 1F shows the trolox equivalents obtained for the treatment with MAP.

The peptides according to the present invention have an excellent activity in preventing, reducing and/or correcting skin imperfections associated with oxidative-stress, such as, skin complexion, pigmentation alterations (such as age spots or solar lentigines), wrinkling and loss in skin density, tone and elasticity due to, for example, reduced amount of collagen or elastic fibers, loss in the structure of the extracellular matrix or structural lipids or DNA damage, increase in skin fragility or increase in inflammatory response, through their demonstrated high antioxidant activity. In addition, given the latter activity, the peptides of the present invention can be used to lighten and/or brighten the skin (providing a uniform colour to the skin and reducing or combating undesired spots, pigmentations and/or irregularities in the colour and/or tone of the skin due to inflammatory responses derived from oxidative stress).

Therefore, in a first embodiment, the present invention refers to a group of peptides which have shown antioxidant, whitening and/or brightening activity.

In a further embodiment, the present invention refers to a composition comprising one of said peptides or a combination thereof.

In an additional embodiment, the present invention refers to the use as a cosmetic of the peptides or the cosmetic compositions of the present invention.

A further embodiment of the present invention refers to the cosmetic use of the peptides or the compositions of the present invention to prevent, reduce and/or remove oxidative stress in the skin and/or brighten the skin.

In another embodiment, the present invention refers to a method to reduce oxidative stress in the skin of a subject, characterized in that it comprises the use of a peptide or a composition of the present invention.

An additional embodiment of the present invention refers to a method to brighten the skin of a subject, characterized in that it comprises the use of a peptide or a composition of the present invention.

The term "non-cyclic aliphatic group" and its plural, as used herein, have the common meaning given in the state of the art to said terms. Therefore, these terms refer to, for example and not restricted to, linear or branched alkyl, alkenyl and alkynyl groups.

The term "alkyl group" and its plural, as used herein, refer to a saturated, linear or branched group, which has between 1 and 24, preferably between 1 and 16, more preferably between 1 and 14, even more preferably between 1 and 12, and even more preferably still between 1, 2, 3, 4, 5 or 6 carbon atoms and which is bound to the rest of the molecule by a simple bond, including, for example and not restricted to, methyl, ethyl, isopropyl, n-propyl, i-propyl, isobutyl, tert-butyl, n-butyl, sec-butyl, n-pentyl, n-hexyl, heptyl, octyl, decyl, dodecyl, lauryl, hexadecyl, octadecyl, amyl, 2-ethylhexyl, 2-methylbutyl, 5-methylhexyl and similar. The alkyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "alkenyl group" and its plural, as used herein, refer to a linear or branched group which has between 2 and 24, preferably between 2 and 16, more preferably between 2 and 14, even more preferably between 2 and 12, even more preferably still 2, 3, 4, 5 or 6 carbon atoms, with one or more carbon-carbon double bonds, preferably with 1, 2 or 3 carbon-carbon double bonds, conjugated or unconjugated, which is bound to the rest of the molecule through a single bond, including, for example and not restricted to, the vinyl, oleyl, linoleyl and similar groups. The alkenyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "alkynyl group" and its plural, as used herein, refer to a linear or branched group which has between 2 and 24, preferably between 2 and 16, more preferably between 2 and 14, even more preferably between 2 and 12, even more preferably still 2, 3, 4, 5 or 6 carbon atoms, with one or more carbon-carbon triple bonds, preferably with 1, 2 or 3 carbon-carbon triple bonds, conjugated or unconjugated, which is bound to the rest of the molecule through a single bond, including, for example and not restricted to, the ethinyl group, 1-propinyl, 2-propinyl, 1-butinyl, 2-butinyl, 3-butinyl, pentinyl, such as 1-pentinyl and similar groups. The alkynyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "alicyclic group" and its plural, as used herein, have the common meaning given in the state of the art to said terms. Hence, these terms are used to refer to, for example and not restricted to, cycloalkyl or cycloalkenyl or cycloalkynyl groups.

The term "cycloalkyl" and its plural, as used herein, refer to a saturated mono- or polycyclic aliphatic group which has between 3 and 24, preferably between 3 and 16, more preferably between 3 and 14, even more preferably between 3 and 12, even more preferably still 3, 4, 5 or 6 carbon atoms and which is bound to the rest of the molecule through a single bond, including, for example and not limited to, cyclopropyl, cyclobutyl, cyclopentyl, cyclohexyl, cycloheptyl, methyl cyclohexyl, dimethyl cyclohexyl, octahydroindene, decahydronaphthalene, dodecahydro-phenalene, adamantyl and similar, and that can optionally be substituted by one or more groups, such as, alkyl, halo, hydroxy, alkoxy, carboxy, carbonyl, cyano, acyl, alkoxy-carbonyl, amino, nitro, mercapto and alkoxythio.

The term "cycloalkenyl" and its plural, as used herein, refer to a non-aromatic mono- or polycyclic aliphatic group which has between 5 and 24, preferably between 5 and 16, more preferably between 5 and 14, even more preferably between 5 and 12, even more preferably still 5 or 6 carbon atoms, with one or more carbon-carbon double bonds, preferably with 1, 2 or 3 carbon-carbon double bonds, conjugated or unconjugated, which is bound to the rest of the molecule through a single bond, including, for example and not restricted to, the cyclopent-1-en-1-yl group and similar groups, and that can optionally be substituted by one or more groups, such as, alkyl, halo, hydroxy, alkoxy, carboxy, carbonyl, cyano, acyl, alkoxy-carbonyl, amino, nitro, mercapto and alkoxythio.

The term "cycloalkynyl" and its plural, as used herein, refer to a non-aromatic mono- or polycyclic aliphatic group which has between 8 and 24, preferably between 8 and 16, more preferably between 8 and 14, even more preferably between 8 and 12, even more preferably still 8 or 9 carbon atoms, with one or more carbon-carbon triple bonds, preferably with 1, 2 or 3 carbon-carbon triple bonds, conjugated or unconjugated, which is bound to the rest of the molecule through a single bond, including, for example and not restricted to, the cyclooct-2-yn-1-yl group and similar, and that can optionally be substituted by one or more groups, such as, alkyl, halo, hydroxy, alkoxy, carboxy, carbonyl, cyano, acyl, alkoxy-carbonyl, amino, nitro, mercapto and alkoxythio.

The term "aryl group" and its plural, as used herein, refer to an aromatic group which has between 6 and 30, preferably between 6 and 18, more preferably between 6 and 10, even more preferably 6 or 10 carbon atoms, which comprises 1, 2, 3 or 4 aromatic rings, bound by a carbon-carbon bond or fused, and which is bound to the rest of the molecule through a single bond, including, for example and not restricted to, phenyl, naphthyl, diphenyl, indenyl, phenanthryl or anthranyl among others. The aryl group can be optionally substituted by one or more substituents, such as, halo, hydroxy, alkoxy, carboxy, carbonyl, cyano, acyl, alkoxy-carbonyl, amino, nitro, mercapto and alkoxythio.

The term "aralkyl group" and its plural, as used herein, refer to an alkyl group substituted by an aromatic group, with between 7 and 24 carbon atoms and including, for example and not restricted to, —($CH_2$)1-6-phenyl, —($CH_2$)1-6-(1-naphtyl), —($CH_2$)1-6-(2-naphtyl), —($CH_2$)1-6-CH(phenyl)$_2$ and similar. The aralkyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "heterocyclic group" and its plural, as used herein, refer to a 3-10 member heterocycyl or hydrocarbon ring, in which one or more of the ring atoms, preferably 1, 2 or 3 of the ring atoms, is a different element to carbon, such as nitrogen, oxygen or sulfur and may be saturated or unsaturated. For the purposes of this invention, the heterocyclyl can be a cyclic, monocyclic, bicyclic or tricyclic system which may include fused ring systems; and the nitrogen, carbon or sulfur atoms can be optionally oxidized in the heterocyclyl radical; the nitrogen atom can optionally be quaternized; and the heterocyclyl radical may be partially or completely saturated or may be aromatic. With increasing preference, the term heterocyclic relates to a 5 or 6 member ring. The heterocyclic groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "heteroarylalkyl group" and its plural, as used herein, refer to an alkyl group substituted with a substituted or unsubstituted aromatic heterocyclyl group, the alkyl group having from 1 to 6 carbon atoms and the aromatic heterocyclyl group between 2 and 24 carbon atoms and from 1 to 3 atoms other than carbon and including, for example and not restricted to, —$(CH_2)$1-6-imidazolyl, —$(CH_2)$1-6-triazolyl, —$(CH_2)$1-6-thienyl, —$(CH_2)$1-6-furyl, —$(CH_2)$1-6-pyrrolidinyl and similar. The heteroarylalkyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The terms "halo" or "halogen", as used in the present document, refer to fluorine, chlorine, bromine or iodine, and its anions are referred to as halides.

As used herein, the term "derivative" and its plural, refer both to cosmetically acceptable compounds, this is, derived from the compound of interest that can be used in the preparation of a cosmetic, and to cosmetically unacceptable derivatives since these may be useful in the preparation of cosmetically acceptable derivatives.

As used in the present document, the term "salt" and its plurals refer to any type of salt from among those known in the state of the art, for example, halide salts, hydroxy acid salts (such as oxyacid salts, acid salts, basic salts and double salts), hydroxo salts, mixed salts, oxy salts or other hydrated salts. This term comprises both cosmetically acceptable salts and cosmetically unacceptable salts, since the latter may be useful in the preparation of cosmetically acceptable salts.

As used in the present document, the term "isomer" and its plural refer to optical isomers, enantiomers, stereoisomers or diastereoisomers. The individual enantiomers or diastereoisomers, as well as their mixtures, may be separated by conventional techniques known in the state of the art.

As used herein, the term "solvate" and its plural refer to any solvate known in the state of the art, such as polar, apolar or amphiphilic solvates, and include any cosmetically acceptable solvate which, when administered or applied to the interested subject (directly or indirectly) provides the compound of interest (the peptide or peptides of the present invention). Preferably, the solvate is a hydrate, a solvate with an alcohol such as methanol, ethanol, propanol or isopropanol, a solvate with an ester such as ethyl acetate, a solvate with an ether such as methyl ether, ethyl ether or THF (tetrahydrofuran) or a solvate with DMF (dimethylformamide), and more preferably a hydrate or a solvate with an alcohol such as ethanol.

In addition, as used herein, the term "amino acid" and its plural include the amino acids codified by the genetic code as well as uncodified amino acids, whether they are natural or not and whether they are D- and L-amino acids. Examples of uncodified amino acids are, without restriction, citrulline, ornithine, sarcosine, desmosine, norvaline, 4-aminobutyric acid, 2-aminobutyric acid, 2-aminoisobutyric acid, 6-aminohexanoic acid, 1-naphthylalanine, 2-naphthylalanine, 2-aminobenzoic acid, 4 aminobenzoic acid, 4-chlorophenylalanine, 2,3-diaminopropionic acid, 2,4 diaminobutyric acid, cycloserine, carnitine, cysteine, penicillamine, pyroglutamic acid, thienylalanine, hydroxyproline, allo-isoleucine, allo-threonine, isonipecotic acid, isoserine, phenylglycine, statin, β-alanine, norleucine, N-methylamino acids, α-amino acids and 1-amino acids, among others, as well as their derivatives. A list of unnatural amino acids is known in the state of the art (see, for example, "Unusual amino acids in peptide synthesis" by D. C. Roberts and F. Vellaccio, The Peptides, Vol. 5 (1983), Chapter VI, Gross E. and Meienhofer J., Eds., Academic Press, New York, USA).

As stated above, in a first aspect, the present invention refers to peptides of formula (I):

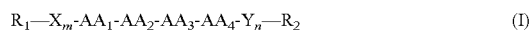

$$R_1-X_m\text{-}AA_1\text{-}AA_2\text{-}AA_3\text{-}AA_4\text{-}Y_n-R_2 \qquad (I)$$

their cosmetically acceptable isomers, salts, solvates and/or derivatives and mixtures thereof, wherein:

X is selected from the group of amino acids with an aliphatic non-polar side-chain;

$AA_1$ is selected from Asp, Glu, His or Thr;

$AA_2$ is selected from the group of aromatic amino acids;

$AA_3$ is selected from Lys, Arg, Phe, Trp or Tyr;

$AA_4$ is selected from Val, lie, Leu, Lys or Arg;

Y is selected from the group of amino acids with an aliphatic non-polar side-chain;

n and m are selected independently of each other from 0 and 1;

$R_1$ is selected from H, substituted or unsubstituted non-cyclic aliphatic, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO— wherein $R_5$ is selected from H, substituted or unsubstituted non-cyclic aliphatic, substituted or unsubstituted alicyclyl, substituted or unsubstituted heterocyclyl, substituted or unsubstituted heteroarylalkyl, substituted or unsubstituted aryl, substituted or unsubstituted aralkyl; and $R_2$ is selected from H, —$NR_3R_4$, —$OR_3$ and —$SR_3$, wherein $R_3$ and $R_4$ are independently selected from H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl.

It is contemplated that the amino acids used or present in the peptides of the present invention are L-amino acids, D-amino acids or combinations thereof. In a preferred embodiment, the amino acids used or present in the peptides of the present invention are L-amino acids.

Preferably, the isomers mentioned above are stereoisomers. It is contemplated that said stereoisomers are enantiomers or diastereoisomers. Hence, in a preferred embodiment of the present invention, the peptide is a racemic mixture, a diastereomeric mixture, a pure enantiomer or a pure diastereoisomer.

In a preferred embodiment, m is 1 and X is Leu.

In another preferred embodiment, n is 1 and Y is Ala.

Hence, in a further preferred embodiment, m is 1 and X is Leu; and n is 1 and Y is Ala.

In another preferred embodiment, m and n are 0.

In an embodiment, $AA_2$ is selected from Tyr, Trp or Phe.

Preferably, $R_1$ is H, acetyl (hereinafter, Ac), palmitoyl, miristoyl, azelaoyl, caffeloyl, azelaic acid, gallic acid, hydroxybenzoic acid, lipoic acid, tartaric acid p-coumaric acid, caffeic acid or ferulic acid, more preferably, $R_1$ is Ac, palmitoyl, azelaic acid, gallic acid, hydroxybenzoic acid, lipoic acid, tartaric acid p-coumaric acid, caffeic acid or ferulic acid, more preferably, $R_1$ is palmitoyl, ferulic acid or Ac, more preferably, $R_1$ is palmitoyl or Ac, and even more preferably $R_1$ is Ac.

Also, preferably, $R_2$ is H or $NH_2$, more preferably $NH_2$.

Therefore, in the most preferred embodiment, $R_1$ is Ac and $R_2$ is H or $NH_2$, more preferably $NH_2$.

In another most preferred embodiment, $R_1$ is ferulic acid and $R_2$ is H or $NH^2$, more preferably $NH_2$.

In another preferred embodiment, the peptide of formula (I) is:

$$R_1\text{-Asp-Tyr-Lys-Val-}R_2; \quad (R_1\text{-SEQ ID NO: 1-}R_2)$$

$$R_1\text{-His-Trp-Phe-Lys-}R_2; \quad (R_1\text{-SEQ ID NO: 2-}R_2)$$

$$R_1\text{-Leu-His-Trp-Phe-Arg-Ala-}R_2, \quad (R_1\text{-SEQ ID NO: 3-}R_2)$$
or $$R_1\text{-Thr-Phe-Phe-Lys-}R_2. \quad (R_1\text{-SEQ ID NO: 4-}R_2)$$

More preferably, the peptide of formula (I) is:

$$\text{Ac-Asp-Tyr-Lys-Val-}R_2; \quad (\text{Ac-SEQ ID NO: 1-}R_2)$$

$$\text{Ac-His-Trp-Phe-Lys-}R_2; \quad (\text{Ac-SEQ ID NO: 2-}R_2)$$

$$\text{Ac-Leu-His-Trp-Phe-Arg-Ala-}R_2; \quad (\text{Ac-SEQ ID NO: 3-}R_2)$$
or $$\text{Palmitoyl-Thr-Phe-Phe-Lys-}R_2. \quad (\text{Palmitoyl-SEQ ID NO: 4-}R_2)$$

Even more preferably, the peptide of formula (I) is:

$$\text{Ac-Asp-Tyr-Lys-Val-}NH_2; \quad (\text{Ac-SEQ ID NO: 1-}NH_2)$$

$$\text{Ac-His-Trp-Phe-Lys-}NH_2; \quad (\text{Ac-SEQ ID NO: 2-}NH_2)$$

$$\text{Ac-Leu-His-Trp-Phe-Arg-Ala-}NH_2; \quad (\text{Ac-SEQ ID NO: 3-}NH_2)$$
or $$\text{Palmitoyl-Thr-Phe-Phe-Lys-}NH_2. \quad (\text{Palmitoyl-SEQ ID NO: 4-}NH_2)$$

In another preferred embodiment, the peptide of formula (I) is:

$$R_1\text{-Asp-Tyr-Lys-Val-}R_2; \quad (R_1\text{-SEQ ID NO: 1-}R_2)$$
or $$R_1\text{-His-Trp-Phe-Lys-}R_2. \quad (R_1\text{-SEQ ID NO: 2-}R_2)$$

In the most preferred embodiment, the peptide of formula (I) is:

$$\text{Ac-Asp-Tyr-Lys-Val-}NH_2; \quad (\text{Ac-SEQ ID NO: 1-}NH_2)$$
or $$\text{Ac-His-Trp-Phe-Lys-}NH_2. \quad (\text{Ac-SEQ ID NO: 2-}NH_2)$$

In a further preferred embodiment, the peptide of formula (I) is:

$$\text{Asp-Tyr-Lys-Val}; \quad (\text{SEQ ID NO: 1})$$
or $$\text{His-Trp-Phe-Lys} \quad (\text{SEQ ID NO: 2})$$

In another preferred embodiment, the peptide of formula (I) is:

$$\text{Leu-His-Trp-Phe-Arg-Ala}. \quad (\text{SEQ ID NO: 3})$$

More preferably, the peptide of formula (I) is:

$$R_1\text{-Leu-His-Trp-Phe-Arg-Ala-}R_2. \quad (R_1\text{-SEQ ID NO: 3-}R_2)$$

Even more preferably, the peptide of formula (I) is:

$$\text{Ac-Leu-His-Trp-Phe-Arg-Ala-}NH_2. \quad (\text{Ac-SEQ ID NO: 3-}NH_2)$$

Also in a preferred embodiment, the peptide of formula (I) is:

$$\text{Ferulic acid-His-Trp-Phe-Lys-}R_2. \quad (\text{Ferulic acid-SEQ ID NO: 2-}R_2)$$

In this embodiment, more preferably, the peptide of formula (I) is:

$$\text{Ferulic acid-His-Trp-Phe-Lys-}NH_2 \quad (\text{Ferulic acid-SEQ ID NO: 2-}NH_2)$$

The activities of the peptides of the present invention, this is, antioxidant and brightening (as demonstrated in the examples included below), demonstrate that said peptides and the compositions comprising them are suitable for the cosmetic prevention, reduction or removal of skin imperfections resulting from oxidation and/or oxidative stress as, for example, skin imperfections appearing as the result of environmental oxidative stress (for example, pollution or UV radiation), undesirable pigmentation of the skin or skin imperfections resulting from aging or photo-aging (for example, skin complexion and/or loss in skin tone and elasticity).

In a second aspect, the present invention refers to a composition comprising a peptide of the present invention, as disclosed herein.

In a preferred embodiment of the present invention, the composition is a cosmetic composition which provides, among others, the above-mentioned cosmetic activities: antioxidant and brightening.

It is contemplated that the cosmetic composition of the present invention comprises one peptide of the present invention or a combination or mixture of the peptides of the present invention.

In an embodiment, the cosmetic composition disclosed above comprises 0.1%-0.0001% (mass/volume; this is, mg/ml) of a peptide of the present invention or a combination of peptides of the present invention. More preferably, said composition comprises 0.1%-0.001% (m/v) of a peptide of the present invention or a combination of peptides of the present invention.

It is contemplated that the cosmetic composition of the present invention also comprises additional cosmetic ingredients usually used in the state of the art as, for example, adjuvants such as stabilizer, solubilizer, vitamin, colorant and perfumery; carriers; and/or other cosmetic active ingredients.

Said additional cosmetic ingredients, must be physically and chemically compatible with the rest of the components of the composition and especially with the peptides of the present invention comprised in the composition of the present invention. Likewise, the nature of said additional cosmetic ingredients must not unacceptably alter the benefits of the compounds of the present invention. Said additional cosmetic ingredients may be of a synthetic or natural origin, such as, for example, plant extracts, or they can be derived from a biofermentation process (see, for example, CTFA Cosmetic Ingredient Handbook, Eleventh Edition (2006)).

It is contemplated that the additional cosmetic ingredients mentioned above comprise those ingredients commonly used in compositions for caring for and/or cleaning skin and/or hair such as, for example, other agents inhibiting melanin synthesis, other whitening or depigmenting agents, anti-ageing agents, agents inhibiting NO-synthase, antioxidants, anti-atmospheric pollution and/or free radical trapping agents, anti-glycation agents, emulsifying agents, emollients, organic solvents, liquid propellants, skin conditioners such as for example wetting agents, moisture retaining substances, alpha hydroxy acids, moisturizers, vitamins, pigments or colorants, dyes, gelling polymers, thickeners, surfactants, softeners, anti-wrinkle agents, agents capable of reducing or eliminating bags under the eyes, exfoliating agents, antimicrobial agents, antifungal agents, bactericides, agents stimulating dermal or epidermal macromolecule synthesis and/or capable of preventing or inhibiting their degradation, such as for example agents stimulating collagen synthesis, agents stimulating elastin synthesis, agents stimulating laminin synthesis, agents inhibiting collagen degradation, agents inhibiting elastin degradation, agents stimulating fibroblast proliferation, agents stimulating keratinocyte proliferation, agents stimulating keratinocyte differentiation, agents stimulating lipid synthesis and synthesis of components of the stratum corneum (ceramides, fatty acids, etc.), dermorelaxing agents, agents stimulating glycosaminoglycan synthesis, DNA repair agents, DNA protecting agents, agents stimulating proteasome activity, anti-pruritus agents, agents for treating sensitive skin, reaffirming agents, astringent agents, sebum production regulating agents, agents stimulating lipolysis, anti-cellulite agents, calming agents, anti-inflammatory agents, agents acting on capillary circulation and/or microcirculation, agents acting on cell metabolism, agents intended to improve the dermo-epidermal junction, preservatives, perfumes, chelating agents, plant extracts, essential oils, marine extracts, agents derived from a biofermentation process, mineral salts, cell extracts and/or solar filters (organic or mineral photoprotective agents active against ultraviolet A and B rays) among others, In an embodiment, therefore, the cosmetic composition of the present invention, also comprises other cosmetic active principles or substances which may exert the same, similar or different cosmetic activities as those disclosed above for the peptides of the present invention.

In a preferred embodiment, the cosmetic composition of the present invention comprises a solar filter or a combination thereof (UVA and/or UVB radiation blockers) to prevent pigmentation, to protect the skin from exposure to the sun or from tanning induced by exposure to the sun, or to increase the capacity of the peptides or compositions of the present invention to reduce the amount of melanin in the skin and their depigmenting action. Examples of solar filters include, among others, p-aminobenzoic acid derivatives, benzylidene camphor derivatives, cinnamic acid derivatives, benzothiazole derivatives, benzimidazole derivatives, benzophenone derivatives, triazine derivatives, salicylic acid derivatives, dibenzoylmethane derivatives, β,β-diphenylacrylate derivatives, as well as nanopigments such as, for example, titanium oxide nanopigments, iron oxide nanopigments, zinc oxide nanopigments, zirconium oxide nanopigments or cerium oxide nanopigments.

It is also contemplated that the cosmetic composition of the present invention comprises a desquamating agent or combinations thereof, capable of promoting exfoliation of the skin for the purpose of obtaining greater efficacy in the depigmenting treatment. Examples of desquamating agents include, among others, alpha hydroxy acids such as, glycolic acid, lactic acid, citric acid, tartaric acid, malic acid and/or mandelic acid among others; beta hydroxy acids such as salicylic acid and derivatives thereof; urea and derivatives thereof; resveratrol and derivatives thereof; N-acetylglucosamine and derivatives thereof; jasmonic acid and derivatives thereof; cinnamic acid; gentisic acid; oligofucoses; *Saphora japonica* extract; and detergents and/or enzymes such as, for example, sutilains, papaya extract, bromelain, pineapple extract, pumpkin extract and/or sweet potato extract, among others.

In addition, the cosmetic composition of the present invention can be formulated as any form usually used in the state of the art as, for example, solution, suspension, emulsion, paste, gel, cream, powder, spray, lotion, oil, liniment, serum, mousse, ointment, bar or pencil including "leave on" and "rinse-off" formulations. The cosmetic composition of the present invention can also be incorporated by means of techniques known in the state of the art to different types of solid accessories such as towelettes, hydrogels, adhesive (or non-adhesive) patches or face masks, or it can be incorporated to different make-up line products such as concealers, make-up foundations, lotions or make-up removal lotions, among others.

It is also contemplated that the cosmetic composition of the present invention or the peptide of the present invention, both as disclosed herein, can also be incorporated in cosmetic sustained release systems and/or carriers such as liposomes, milliparticles, microparticles and nanoparticles, as well as in sponges, vesicles, micelles, millispheres, microspheres, nanospheres, lipospheres, millicapsules, microcapsules and nanocapsules, as well as in microemulsions and nanoemulsions, for the purpose of obtaining greater penetration of the active ingredient.

In a preferred embodiment, the cosmetic composition of the present invention is suited or adapted to be applied topically, in the face and/or the body of a subject, more preferably of a human.

In a third aspect, the present invention relates to the use as a cosmetic of the peptides or the cosmetic compositions of the present invention to prevent, reduce or remove oxidative stress in the skin and/or brighten the skin of a subject.

In an embodiment, said use as a cosmetic is to prevent, reduce or remove skin imperfections resulting from oxidation and/or oxidative stress, more preferably, to prevent, reduce or remove skin imperfections appearing as the result of environmental oxidative stress (for example, pollution or UV radiation), undesirable pigmentation of the skin or skin imperfections resulting from aging or photo-aging.

In a preferred embodiment, such skin imperfections are, skin complexion, pigmentation alterations (such as age spots or solar lentigines), wrinkling and/or loss in skin tone and elasticity due to, for example, loss in the structure of the extracellular matrix, increase in skin fragility and/or increase in inflammatory response (Baumann, L., *Skin ageing and its treatment*, J. Pathol., 2007; 211:241-251).

Hence, in a preferred embodiment, the above-mentioned use as a cosmetic of the peptides or cosmetic compositions of the present invention is to prevent, reduce or remove signs of skin aging and/or photo-aging.

In another preferred embodiment, the use as a cosmetic of the peptides or cosmetic compositions of the present invention is used to prevent, reduce or remove pigmentation alterations.

Also in a preferred embodiment, the subject is a human.

It is contemplated that in the use as a cosmetic of the present invention as disclosed above, the peptide or the composition of the present invention is used in combination with one or more additional active principles and/or compositions. Said one or more active principles and/or compositions may be used before, together or after the peptide or composition of the present invention.

In a preferred embodiment, in the use of the present invention as disclosed above, the peptide and/or the cosmetic composition of the present invention is applied topically, in the face and/or body of the subject, more preferably of a human.

In a fourth aspect, the present invention refers to the cosmetic use of the peptides or the cosmetic compositions of the present invention, as described above, to prevent, reduce or remove oxidative stress in the skin and/or brighten the skin of a subject.

The prevention, reduction or removal of oxidative stress and/or the brightening of the skin allows the prevention, reduction or removal of skin imperfections appearing as the result of environmental oxidative stress (for example, pollution or UV radiation).

Examples of such skin imperfections are, skin complexion, pigmentation alterations (such as age spots or solar lentigines), wrinkling and/or loss in skin tone and elasticity due to, for example, loss in the structure of the extracellular matrix, increase in skin fragility and/or increase in inflammatory response (Baumann, L. *Skin ageing and its treatment*, J. Pathol., 2007; 211:241-251).

Hence, in a preferred embodiment, the cosmetic use of the peptides or compositions of the present invention is to prevent, reduce or remove signs of skin aging and/or photo-aging.

In another preferred embodiment, the cosmetic use of the peptides or compositions of the present invention is used to prevent, reduce or remove pigmentation alterations.

Also in a preferred embodiment, the subject is a human.

It is contemplated that in the cosmetic use of the present invention as disclosed above, the peptide or the composition of the present invention is used in combination with one or more additional active principles and/or compositions. Said one or more active principles and/or compositions may be used before, together or after the peptide or composition of the present invention.

In a preferred embodiment, in the cosmetic use of the present invention as disclosed above, the peptide and/or the cosmetic composition of the present invention is applied topically, in the face and/or body of the subject, more preferably of a human.

In a fifth aspect, the present invention refers to a method to prevent, reduce or remove oxidative stress in the skin of a subject, characterized in that it comprises the use of a peptide or a cosmetic composition of the present invention.

In a preferred embodiment, the subject is a human.

It is contemplated that the peptide or composition of the present invention is used in the method of the present invention by direct application to the zone of the skin of the human body. In a preferred embodiment, the peptide or composition of the present invention is applied in the form of solution, suspension, emulsion, paste, gel, cream, powder, spray, lotion, oil, liniment, serum, mousse, ointment, bar or pencil including "leave on" and "rinse-off" formulations. As stated above, it is also contemplated that the peptide or composition of the present invention can also be incorporated by means of techniques known in the state of the art to different types of solid accessories such as towelettes, hydrogels, adhesive (or non-adhesive) patches or face masks, or it can be incorporated to different make-up line products such as concealers, make-up foundations, lotions or make-up removal lotions, among others; and, hence used in any of said forms in the method of the present invention.

As stated above, the method disclosed above is a cosmetic method with cosmetic effect.

In the method of the present invention, the prevention, reduction or removal of oxidative stress in the skin has the above-mentioned activities, effects and/or uses.

It is contemplated that in the method of the present invention as disclosed above, the peptide or the composition of the present invention is used in combination with one or more additional active principles and/or compositions. Said one or more active principles and/or compositions may be used before, together or after the peptide or composition of the present invention.

In a preferred embodiment, in the method of the present invention as disclosed above, the peptide and/or the cosmetic composition of the present invention is applied topically, in the face and/or body of the subject, more preferably of a human.

In a final aspect, the present invention refers to a method to brighten the skin of a subject, characterized in that it comprises the use of a peptide or a composition of the present invention.

In a preferred embodiment, the subject is a human.

It is contemplated that the peptide or composition of the present invention is used in the method of the present invention by direct application to the zone of the skin of the human body. In a preferred embodiment, the peptide or composition of the present invention is applied in the form of solution, suspension, emulsion, paste, gel, cream, powder, spray, lotion, oil, liniment, serum, mousse, ointment, bar or pencil including "leave on" and "rinse-off" formulations. As stated above, it is also contemplated that the peptide or composition of the present invention can also be incorporated by means of techniques known in the state of the art to different types of solid accessories such as towelettes, hydrogels, adhesive (or non-adhesive) patches or face masks, or it can be incorporated to different make-up line products such as concealers, make-up foundations, lotions or make-up removal lotions, among others; and, hence used in any of said forms in the method of the present invention.

As stated above, the method disclosed above is a cosmetic method with cosmetic effect.

In the method of the present invention, the prevention, reduction or removal of oxidative stress in the skin has the above-mentioned effects and/or uses.

It is contemplated that in the method of the present invention as disclosed above, the peptide or the composition of the present invention is used in combination with one or more additional active principles and/or compositions. Said one or more active principles and/or compositions may be used before, together or after the peptide or composition of the present invention.

In a preferred embodiment, in the method of the present invention as disclosed above, the peptide and/or the cosmetic composition of the present invention is applied topically, in the face and/or body of the subject, more preferably of a human.

As already noted above, the peptides of the present invention (and, hence, also the cosmetic compositions of the present invention) have shown a wide spectrum antioxidant and/or brightening activities as they have exhibited said activities under a wide variety of conditions. Hence, said peptides and compositions comprising them are suited to be used in cosmetics to prevent, reduce or remove skin imperfections generated by oxidation or oxidative stress under a wide variety of conditions.

To allow a better understanding, the present invention is described in more detail below with reference to the enclosed drawings, which are presented by way of example, and with reference to illustrative and non-limitative examples.

FIG. 1 shows the antioxidant power of Ac-SEQ ID NO: 1-$NH_2$, Ac-SEQ ID NO: 2-$NH_2$, Ac-SEQ ID NO: 3-$NH_2$ and Ferulic acid-SEQ ID NO: 2-$NH_2$ in the form of trolox equivalents (see example 9). FIG. 1(A) shows the trolox equivalents obtained for the treatment with Ac-SEQ ID NO: 1-$NH_2$ in the three concentrations tested, columns from left to right (x-axis): 0.01 mg/ml, 0.05 mg/ml and 0.1 mg/ml. FIG. 1(B) shows the trolox equivalents obtained for the treatment with Ac-SEQ ID NO: 2-$NH_2$ in the three corresponding concentrations tested, columns from left to right (x-axis): 0.05 mg/ml, 0.1 mg/ml and 0.5 mg/ml. FIG. 1(C) shows the trolox equivalents obtained for the treatment with Ac-SEQ ID NO: 3-$NH_2$ in the three corresponding concentrations tested, columns from left to right (x-axis): 0.01 mg/ml, 0.05 mg/ml and 0.1 mg/ml. FIG. 1(D) shows the trolox equivalents obtained for the treatment with Ferulic acid-SEQ ID NO: 2-$NH_2$ in the three corresponding concentrations tested, columns from left to right (x-axis): 0.01 mg/ml, 0.05 mg/ml and 0.1 mg/ml. As positive controls of the assay, ascorbic acid 2-glucoside (hereinafter, AA-2G) and magnesium ascorbyl phosphate (hereinafter, MAP) were tested. FIG. 1(E) shows the trolox equivalents obtained for the treatment with AA-2G in the three corresponding concentrations tested, columns from left to right (x-axis): 0.01 mg/ml, 0.05 mg/ml and 0.1 mg/ml. FIG. 1(F) shows the trolox equivalents obtained for the treatment with MAP in the three corresponding concentrations tested, columns from left to right (x-axis): 0.01 mg/ml, 0.05 mg/ml and 0.1 mg/ml. For FIGS. 1(A) to 1(F), the y-axis shows the trolox equivalents in $\mu M$.

Figure 2:
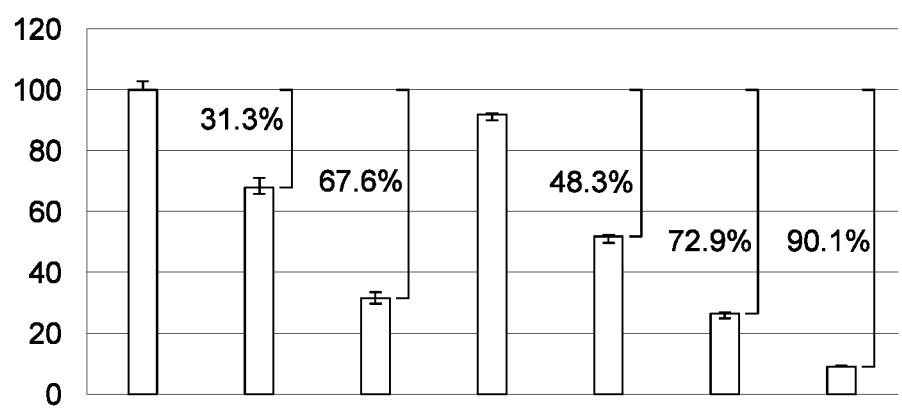
FIG. 2 shows the antioxidant activity of Ferulic acid-SEQ ID NO: 2-NH$_2$.

FIG. 2 shows the antioxidant activity of Ferulic acid-SEQ ID NO: 2-$NH_2$ at four concentrations and the reference compound ascorbic acid at two concentrations, assessed by means of the 2,2-diphenyl-1-picrylhydrazyl (hereinafter, DPPH) assay and normalized on the basis of the control sample (as explained in example 10). Columns from left to right in the x-axis correspond to: control (no peptide added); ascorbic acid at 30 $\mu M$ and 60 $\mu M$, respectively; and concentrations 0.01 mg/mL, 0.05 mg/mL, 0.1 mg/mL and 0.5 mg/mL of Ferulic acid-SEQ ID NO: 2-$NH_2$. The y-axis shows the antioxidant activity (% of DPPH reduction) versus the control condition (no peptide added).

Figure 3A:
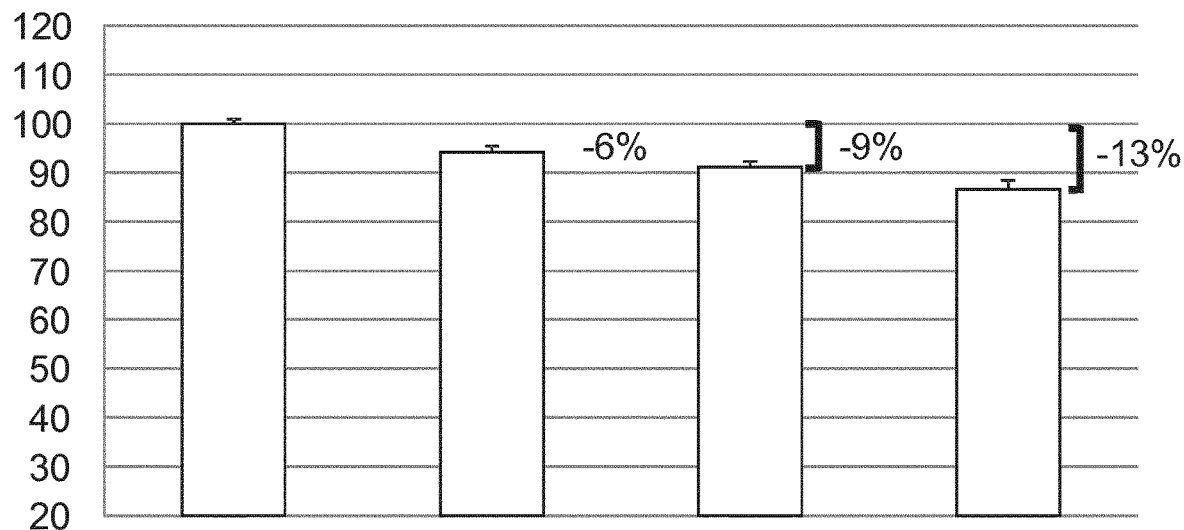
FIG. 3A shows the results of percentage of lipid peroxidation obtained for the treatment with Ac-SEQ ID NO: 1-NH$_2$.
Figure 3B:
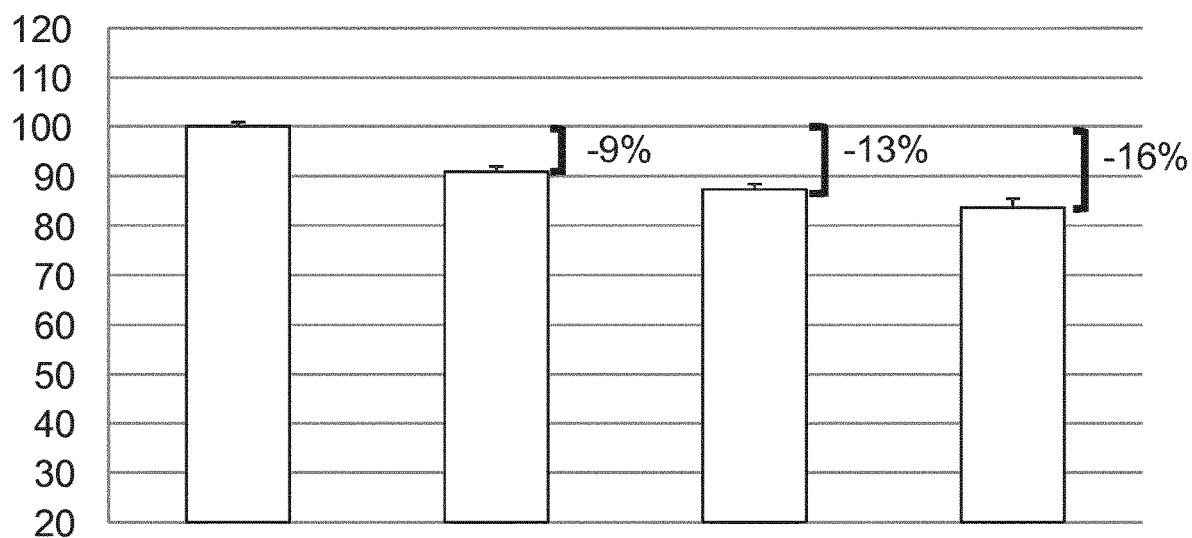
FIG. 3B shows the results of percentage of lipid peroxidation obtained for the treatment with Ac-SEQ ID NO: 2-NH$_2$.

FIG. 3 shows the percentage of lipid peroxidation normalized on the basis of the control sample (as explained in example 11), this is, setting the percentage of lipid peroxidation in the control sample as 100% and then performing the comparison with the rest of the samples. FIG. 3(A) shows the results of percentage of lipid peroxidation obtained for the treatment with Ac-SEQ ID NO: 1-$NH_2$ in the three concentrations tested. Columns from left to right in the x-axis in FIG. 3(A) correspond to: control and treatments with Ac-SEQ ID NO: 1-$NH_2$ concentrations of 0.01 mg/ml, 0.05 mg/ml and 0.1 mg/ml, respectively. FIG. 3(B) shows the results of percentage of lipid peroxidation obtained for the treatment with Ac-SEQ ID NO: 2-$NH_2$ in the three corresponding concentrations tested. Columns from left to right in the x-axis in FIG. 3(B) correspond to: control and treatments with Ac-SEQ ID NO: 2-$NH_2$ concentrations of 0.01 mg/ml, 0.05 mg/ml and 0.1 mg/ml, respectively. For both FIGS. 3(A) and 3(B), the y-axis shows the percentage of lipid peroxidation versus the lipid peroxidation observed in the positive control sample.

Figure 4A:
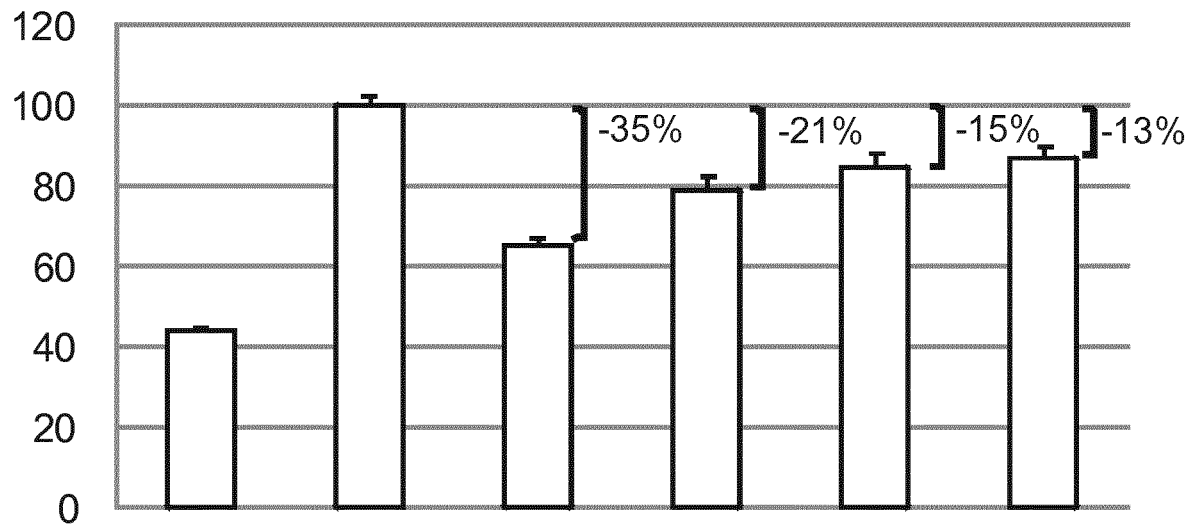
FIG. 4A shows the results of the percentage of reactive oxygen species obtained for the treatment with Ac-SEQ ID NO: 1-NH$_2$.
Figure 4B:
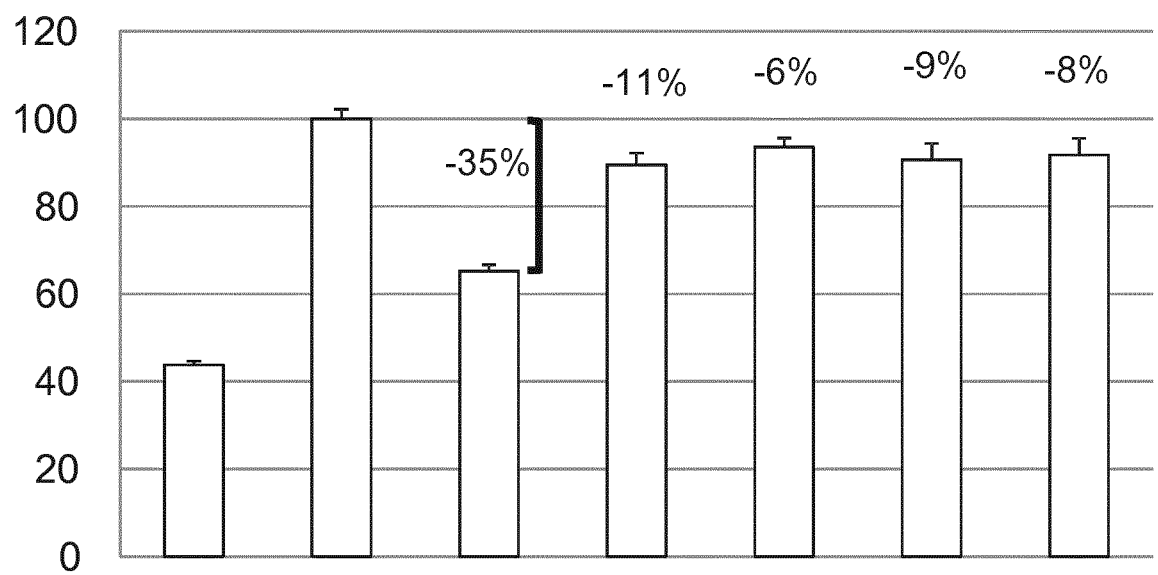
FIG. 4B shows the results of the percentage of reactive oxygen species obtained for the treatment with Ac-SEQ ID Na 2-NH$_2$.

FIG. 4 shows the percentage of reactive oxygen species (induced by hydrogen peroxide) in comparison with the positive control sample (sample treated only with 100 $\mu M$ of hydrogen peroxide, as explained in example 12), this is, setting the percentage of reactive oxygen species in the positive control sample as 100% and then performing the comparison with the rest of the samples. FIG. 4(A) shows the results of the percentage of reactive oxygen species obtained for the treatment with Ac-SEQ ID NO: 1-$NH_2$ in the three concentrations tested. Columns from left to right in the x-axis of FIG. 4(A) correspond to: basal state (cells to which no treatment is applied), positive control, negative control of oxidation (sample treated with 1 mM ascorbic acid) and treatments with Ac-SEQ ID NO: 1-$NH_2$ concentrations of 0.001 mg/ml, 0.005 mg/ml and 0.01 mg/ml, respectively. FIG. 4(B) shows the results of the percentage of reactive oxygen species obtained for the treatment with Ac-SEQ ID NO: 2-$NH_2$ in the four corresponding concentrations tested. Columns from left to right in the x-axis of FIG. 3(B) correspond to: basal state (cells to which no treatment is applied), positive control, negative control (sample treated with 1 mM ascorbic acid) and treatments with Ac-SEQ ID NO: 2-$NH_2$ concentrations of 0.001 mg/ml, 0.005 mg/ml, 0.01 mg/ml and 0.05 mg/ml, respectively. For both FIGS. 4(A) and 4(B), the y-axis shows the percentage of reactive oxygen species versus the reactive oxygen species observed in the positive control sample.

Figure 5:
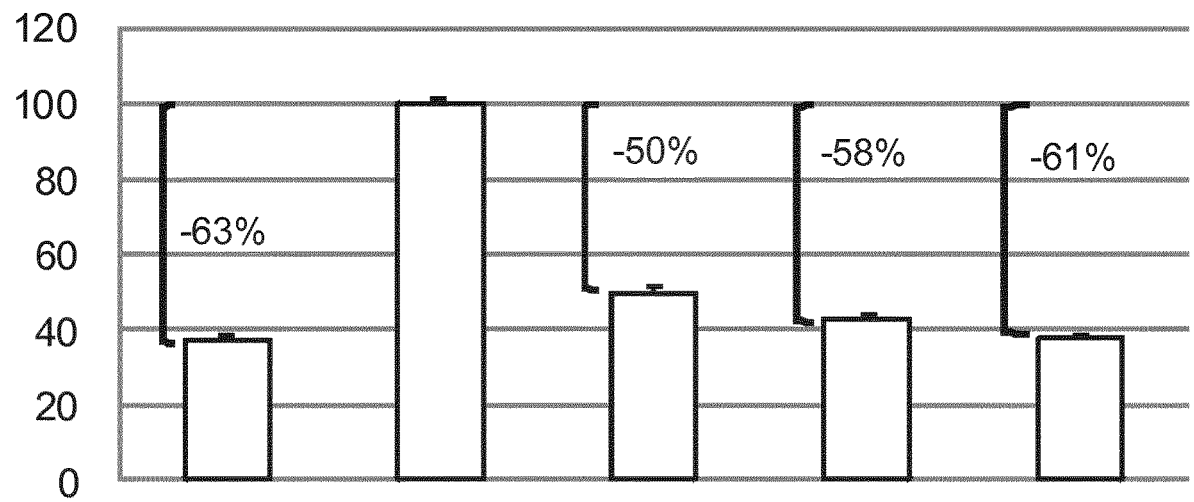
FIG. 5 shows the percentage of advanced glycation end-products (induced by heavy metals) obtained for the treatment with Ac-SEQ ID NO: 1-NH$_2$.

FIG. 5 shows the percentage of advanced glycation end-products (induced by heavy metals) obtained for the treatment with Ac-SEQ ID NO: 1-$NH_2$, in comparison with the control sample (sample treated only with 300 $\mu M$ of heavy metals, as explained in example 13), this is, setting the percentage of advanced glycation end-products in the control sample as 100% and then performing the comparison with the rest of the samples. The x-axis shows the samples tested, this is, columns from left to right: basal state (cells to which no treatment is applied), positive control and the three Ac-SEQ ID NO: 1-NH$_2$ concentrations tested, 0.01 mg/ml, 0.05 mg/ml and 0.1 mg/ml, respectively. The y-axis shows the percentage of Advanced Glycation End Products versus the Advanced Glycation End products observed in the control sample.

Figure 6:
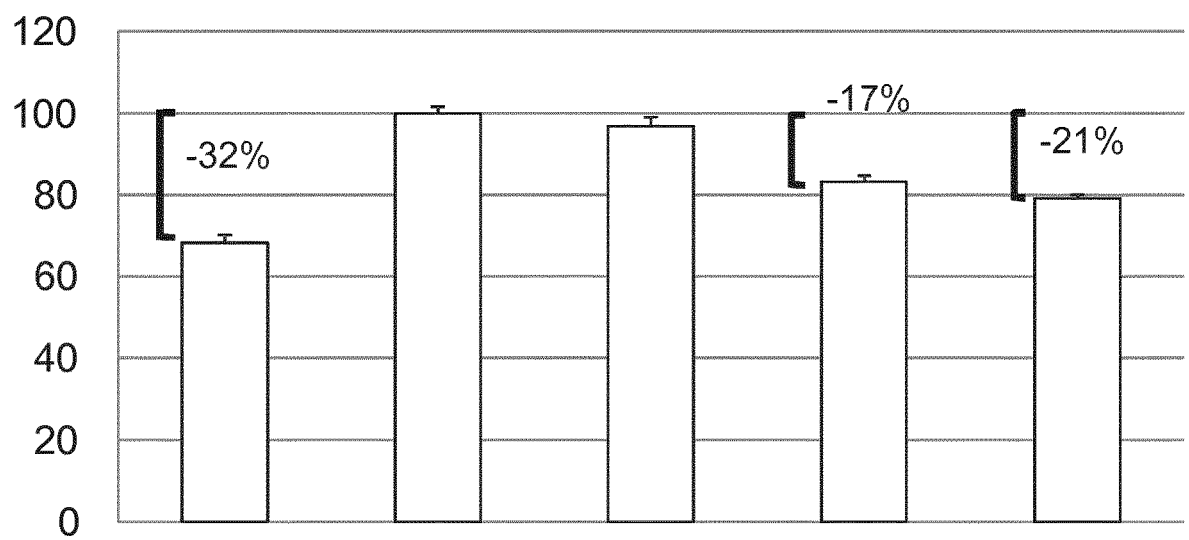
FIG. 6 shows the protection of DNA oxidation in comparison with the control sample.

FIG. 6 shows the protection of DNA oxidation (induced by synthetic smoke) in comparison with the control sample (sample treated only with synthetic smoke, as explained in example 14). To this end, FIG. 6 shows the percentage of 8-hydroxydeoxyguanosine (as measure of DNA oxidation) obtained for the treatment with Ac-SEQ ID NO: 1-NH$_2$ in comparison or normalized with that of the control sample (setting the percentage of the control sample as 100% and then performing the comparison with the rest of the samples). The x-axis shows, from left to right: basal state (cells to which no treatment is applied), positive control and the three Ac-SEQ ID NO: 1-NH$_2$ concentrations tested, 0.01 mg/ml, 0.05 mg/ml and 0.1 mg/ml, respectively. The y-axis shows the percentage of 8-hydroxydeoxyguanosine versus the 8-hydroxydeoxyguanosine observed in the control sample.

Figure 7:
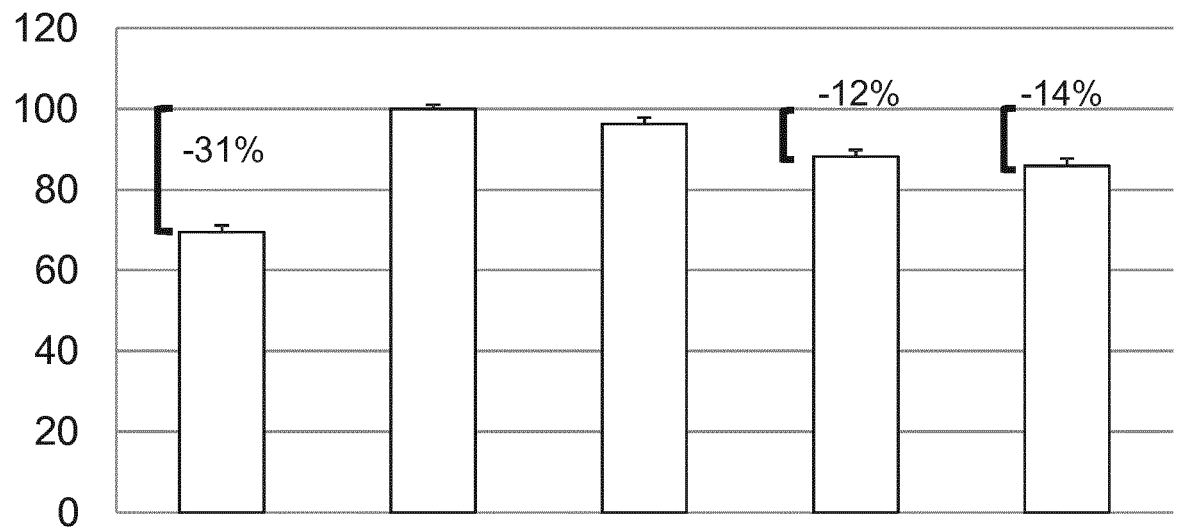
FIG. 7 shows the protection of lipoxidation in comparison with the control sample.

FIG. 7 shows the protection of lipoxidation (induced by synthetic smoke) in comparison with the control sample (sample treated only with synthetic smoke, as explained in example 14). To this end, FIG. 7 shows the percentage of MDA (as measure of lipoxidation) obtained for the treatment with Ac-SEQ ID NO: 1-NH$_2$ in comparison with that of the control sample (setting the percentage of the control sample as 100% and then performing the comparison with the rest of the samples). The x-axis shows, from left to right: basal state (cells to which no treatment has been applied), control and the three concentrations tested for Ac-SEQ ID NO: 1-NH$_2$, this is, 0.01 mg/ml, 0.05 mg/ml and 0.1 mg/ml, respectively. The y-axis shows the percentage MDA versus the MDA observed in the control sample.

Figure 8:
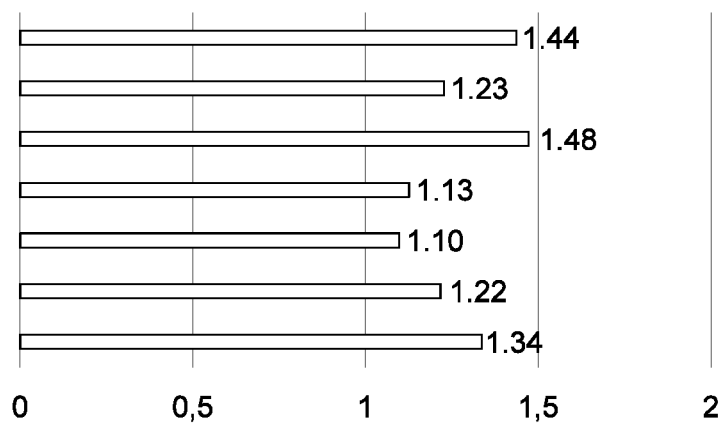
FIG. 8 shows the effect of Ac-SEQ ID NO: 1-NH$_2$ on the gene expression profile of HEKa cells after treatment with a peptide concentration of 0.05 mg/mL.

FIG. 8 shows the effect of Ac-SEQ ID NO: 1-NH$_2$ on the gene expression profile of HEKa cells after treatment with a peptide concentration of 0.05 mg/mL. Changes in gene expression levels are represented as a positive or negative fold-change with regard to the basal control (untreated cells). Bars from top to bottom in the y-axis refer to: CYP2R1 (Vitamin D 25-hydroxylase), NFE2L2 (Nuclear factor-like 2), HMOX1 (Heme oxygenase-1), GSTP1 (Glutathione S-transferase P), GSS (Glutathione synthetase), GPX1 (Glutathione peroxidase) and TRX (Thioredoxin). The x-axis refers to fold change versus or with regard to the basal control. A negative fold change means that the corresponding gene is downregulated; and a positive fold change means that the corresponding gene is upregulated.

Figure 9A:
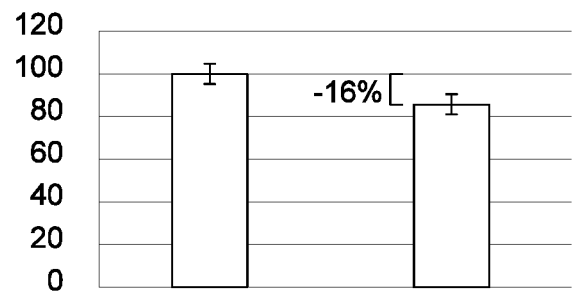
FIG. 9A show the percentage of epidermal surface occupied by AhR on human skin explants, treated or not with Ac-SEQ ID NO: 1-NH$_2$ after exposure to pollutants.
Figure 9B:
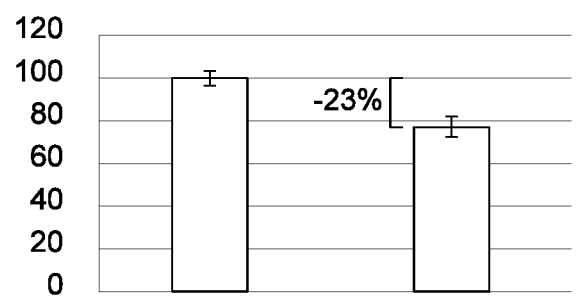
FIG. 9B show the percentage of epidermal surface occupied by heme oxygenase-1 (hereinafter HO-1) on human skin explants, treated or not with Ac-SEQ ID NO: 1-NH$_2$ after exposure to pollutants.
Figure 9C:
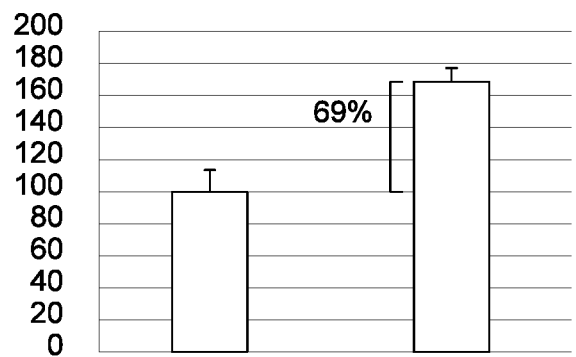
FIG. 9C shows the percentage of epidermal surface occupied by HO-1, of explants treated or not with Ac-SEQ ID NO: 1-NH$_2$ with no exposure to pollutants.

FIG. 9 shows the antioxidant and anti-pollutant efficacy of peptide Ac-SEQ ID NO: 1-NH$_2$ on human skin explants. FIGS. 9(A) and 9(B) show the percentage of epidermal surface occupied by AhR (FIG. 9(A)) and heme oxygenase-1 (hereinafter, HO-1) (FIG. 9(B)) on human skin explants, previously treated or not with peptide Ac-SEQ ID NO: 1-NH$_2$, after exposure to a mixture of pollutants (heavy metals and hydrocarbons), while FIG. 9(C) shows the percentage of epidermal surface occupied by HO-1, of explants treated or not with Ac-SEQ ID NO: 1-NH$_2$ with no exposure to pollutants. The x-axis shows, for FIGS. 9(A) and 9(B), from left to right: untreated explants exposed to the mixture of pollutants and explants exposed to the mixture of pollutants and treated with Ac-SEQ ID NO: 1-NH$_2$. On its side, the x-axis for FIG. 9(C) shows, from left to right, untreated explants and explants treated with Ac-SEQ ID NO: 1-NH$_2$. The y-axis shows the percentage of surface occupied by AhR (FIG. 9(A)) and HO-1 (FIGS. 9(B) and 9(C)), establishing as 100% the value obtained for the untreated but exposed to the mixture of pollutants explants for FIGS. 9(A) and 9(B), and untreated and unexposed explants for FIG. 9(C).

Figure 10:
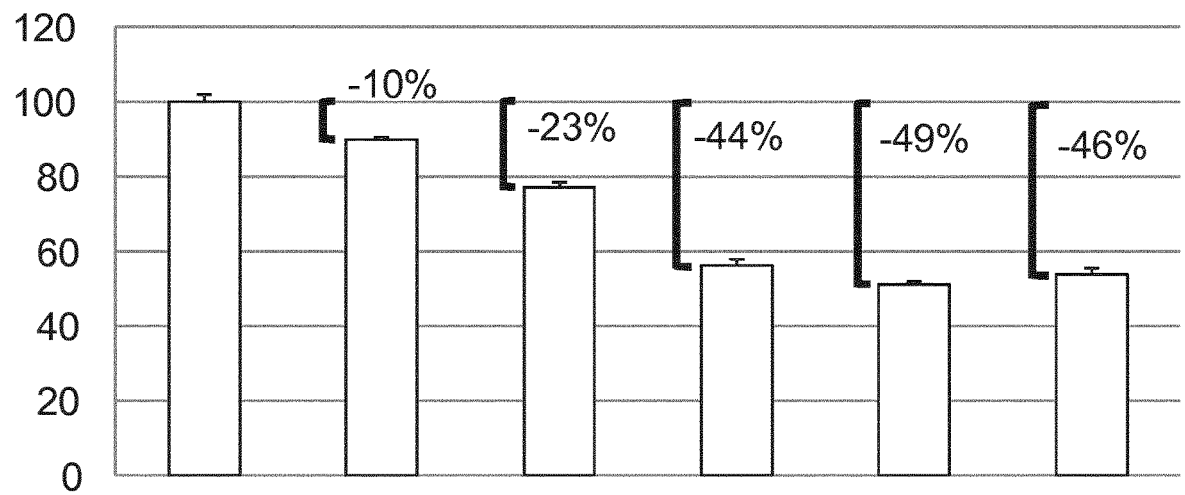
FIG. 10 shows the brightening efficacy of Ac-SEQ ID NO: 1-NH$_2$.

FIG. 10 shows the brightening efficacy of Ac-SEQ ID NO: 1-NH$_2$. To this end, FIG. 10 shows the percentage of melanin per cell in comparison with the melanin per cell present in the basal state (cells to which no treatment has been applied) (setting the percentage of the basal state as 100% and then performing the comparison with the rest of the samples), obtained for the treatment with Ac-SEQ ID NO: 1-NH$_2$. Two concentrations of kojic acid were used as positive control. The x-axis shows, from left to right: basal state, 10 µM kojic acid, 50 µM kojic acid and the three concentrations of Ac-SEQ ID NO: 1-NH$_2$ tested, 0.01 mg/ml (17.7 µM), 0.05 mg/ml (88.5 µM) and 0.1 mg/ml (177.1 µM), respectively. The y-axis shows the percentage of melanin per cell (stablishing as 100% the value obtained for the basal state).

Figure 11:
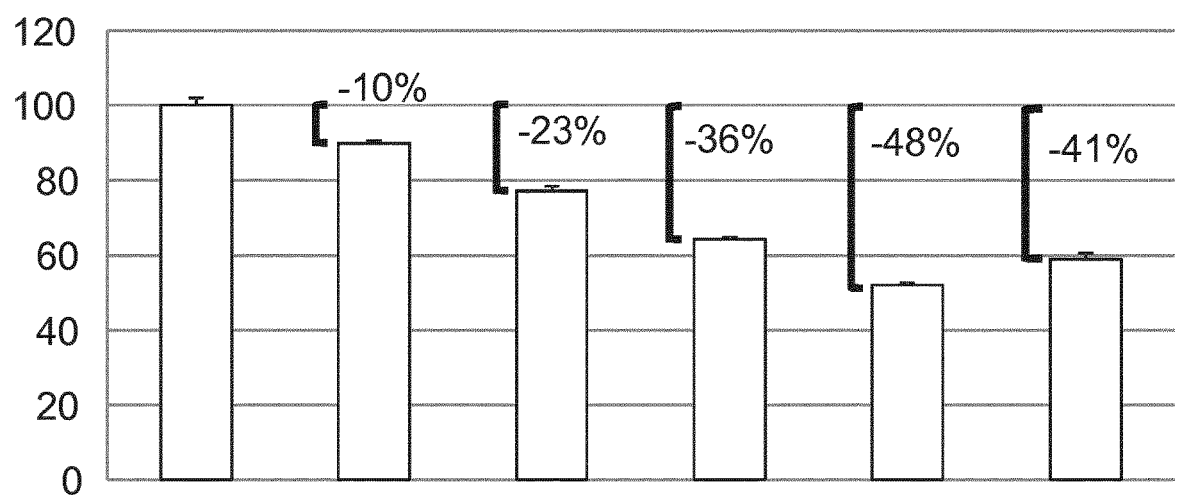
FIG. 11 shows the brightening efficacy of Ac-SEQ ID NO: 2-NH$_2$.

FIG. 11 shows the brightening efficacy of Ac-SEQ ID NO: 2-NH$_2$. To this end, FIG. 11 shows the percentage of melanin per cell in comparison with the melanin per cell present in the basal state (cells to which no treatment has been applied) (setting the percentage of the basal state as 100% and then performing the comparison with the rest of the samples), obtained for the treatment with Ac-SEQ ID NO: 2-NH$_2$. Two concentrations of kojic acid were used as positive control. The x-axis shows, from left to right: basal state, 10 µM kojic acid, 50 µM kojic acid and the three concentrations of Ac-SEQ ID NO: 2-NH$_2$ tested, 0.01 mg/ml (15.2 µM), 0.05 mg/ml (76 µM) and 0.1 mg/ml (152 µM), respectively. The y-axis shows the percentage of melanin per cell (stablishing as 100% the value obtained for the basal state).

Figure 12:
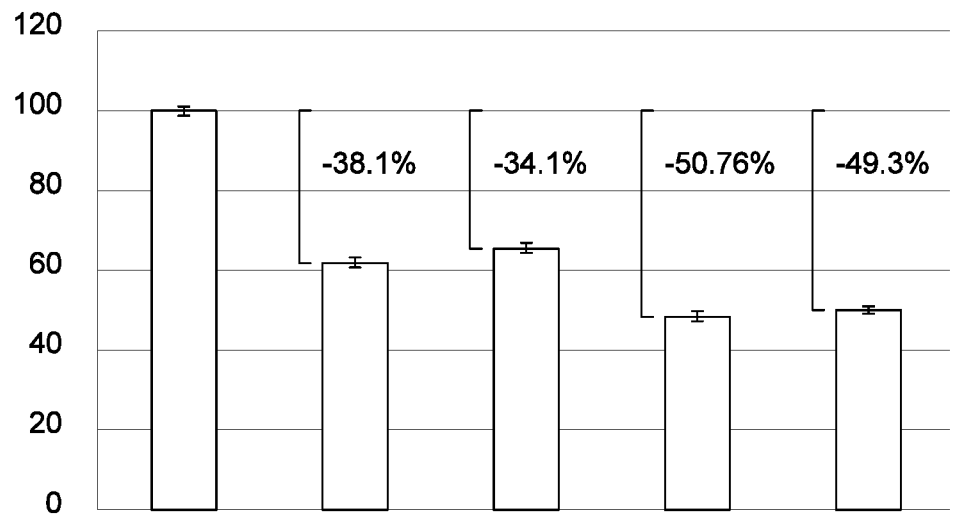
FIG. 12 shows the brightening efficacy of Ac-SEQ ID NO: 3-NH$_2$.

FIG. 12 shows the brightening efficacy of Ac-SEQ ID NO: 3-NH$_2$. To this end, FIG. 12 shows the percentage of melanin per cell in comparison with the melanin per cell present in the basal state (cells to which no treatment has been applied) (setting the percentage of the basal state as 100% and then performing the comparison with the rest of the samples), obtained for the treatment with Ac-SEQ ID NO: 3-NH$_2$. Kojic acid was used as positive control. The x-axis shows, from left to right: basal state, 70 µM kojic acid and the three concentrations of Ac-SEQ ID NO: 3-NH$_2$ tested, this is, 0.01 mg/ml (11.5 µM), 0.05 mg/ml (57.5 µM) and 0.1 mg/ml (115 µM), respectively. The y-axis shows the percentage of melanin per cell (stablishing as 100% the value obtained for the basal state).

Figure 13:
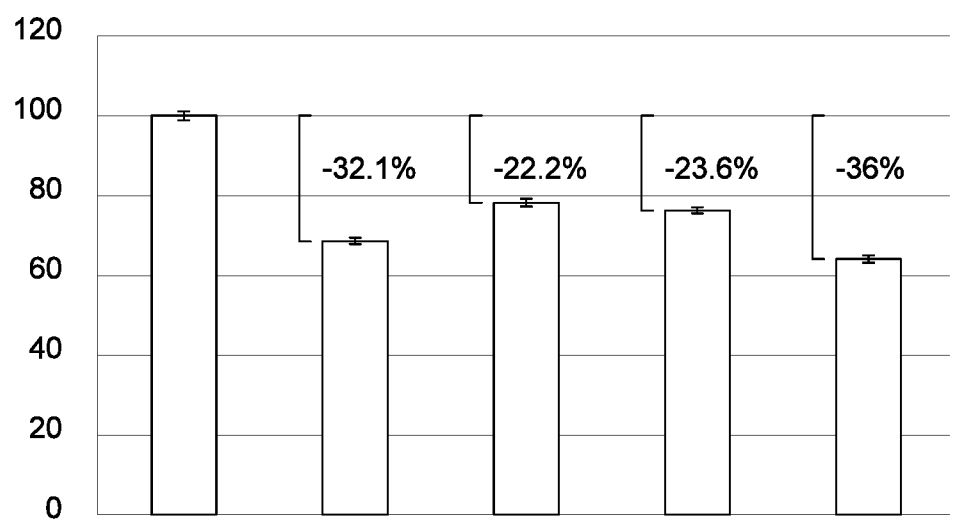
FIG. 13 shows the brightening efficacy of Ferulic acid-SEQ ID NO: 2-NH$_2$.

FIG. 13 shows the brightening efficacy of Ferulic acid-SEQ ID NO: 2-NH$_2$. To this end, FIG. 13 shows the percentage of melanin per cell in comparison with the melanin per cell present in the basal state (cells to which no treatment has been applied) (setting the percentage of the basal state as 100% and then performing the comparison with the rest of the samples), obtained for the treatment with Ferulic acid-SEQ ID NO: 2-NH$_2$. Kojic acid was used as positive control. The x-axis shows, from left to right: basal state, 70 µM kojic acid and the three concentrations of Ferulic acid-SEQ ID NO: 2-NH$_2$ tested, this is, 0.005 mg/mL (6.3 µM), 0.01 mg/ml (12.6 µM) and 0.05 mg/ml (63

μM), respectively. The y-axis shows the percentage of melanin per cell (stablishing as 100% the value obtained for the basal state).

Figure 14:
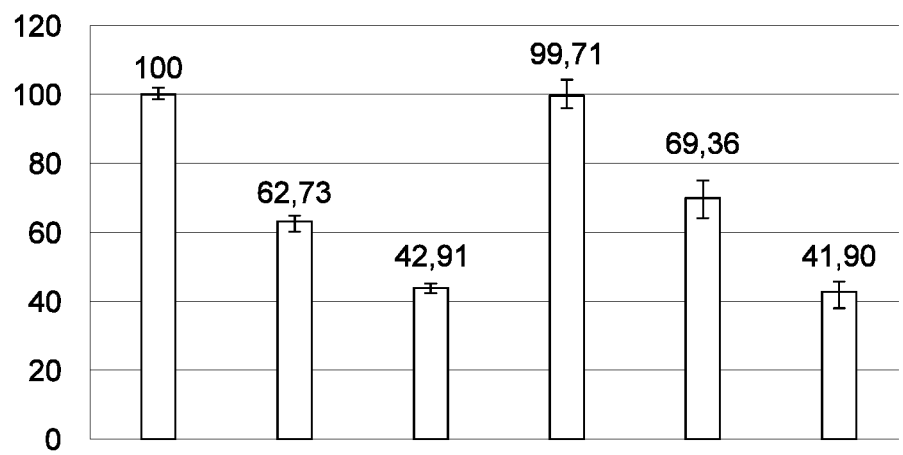
FIG. 14 shows the inhibitory effect of peptide Ac-SEQ ID NO: 3-NH$_2$ on mushroom tyrosinase activity in tubo.

FIG. 14 shows the inhibitory effect of peptide Ac-SEQ ID NO: 3-$NH_2$ on mushroom tyrosinase activity in tubo. Results are shown as percentage of mushroom tyrosinase inhibition compared to basal (non-treated cells). Kojic acid was used as positive control. The x-axis shows, from left to right: basal state, 400 μM and 800 μM of kojic acid and the three concentrations of Ac-SEQ ID NO: 3-$NH_2$ tested, this is 0.1 mg/mL, 0.5 mg/mL and 1 mg/mL. The y-axis shows mushroom tyrosinase percentage activity (stablishing as 100% the value obtained for the basal state).

Figure 15:
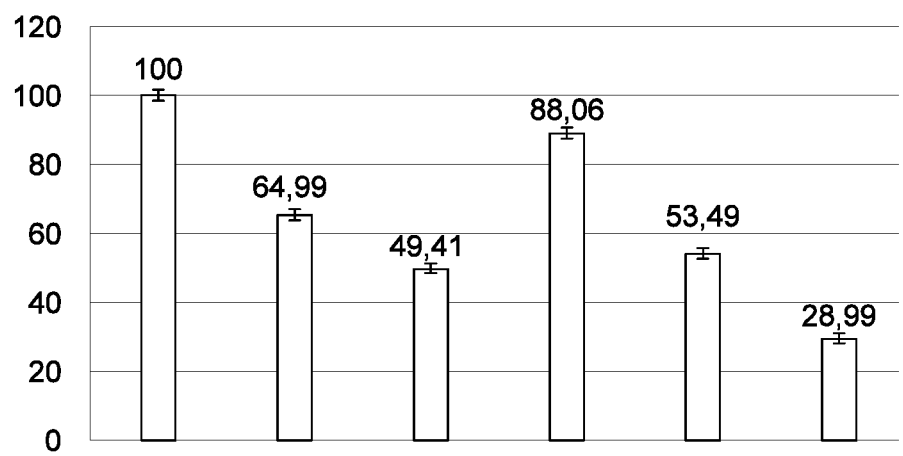
FIG. 15 shows the inhibitory effect of peptide Ferulic acid-SEQ ID NO: 2-NH$_2$ on mushroom tyrosinase activity in tubo.

FIG. 15 shows the inhibitory effect of peptide Ferulic acid-SEQ ID NO: 2-$NH_2$ on mushroom tyrosinase activity in tubo. Results are shown as percentage of mushroom tyrosinase inhibition compared to basal (non-treated wells). Kojic acid was used as positive control. The x-axis shows, from left to right: basal state, 400 μM and 800 μM of kojic acid and the three concentrations of Ferulic acid-SEQ ID NO: 2-$NH_2$ tested, this is, 0.05 mg/mL, 0.1 mg/mL and 0.5 mg/mL. The y-axis shows mushroom tyrosinase percentage activity (stablishing as 100% the value obtained for the basal state).

Figure 16A:
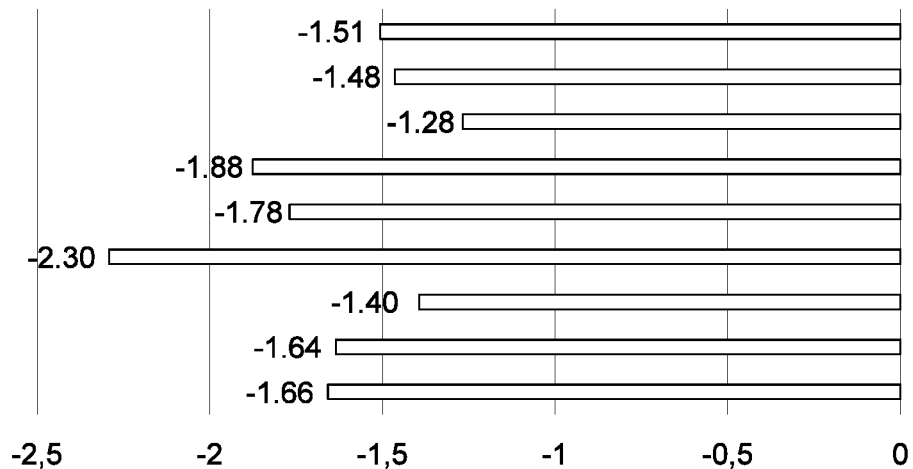
FIG. 16A shows the effect of Ac-SEQ ID NO: 3-NH$_2$ on the gene expression profile of HEMn cells after 11-day treatment with a peptide concentration of 0.1 mg/mL.
Figure 16B:
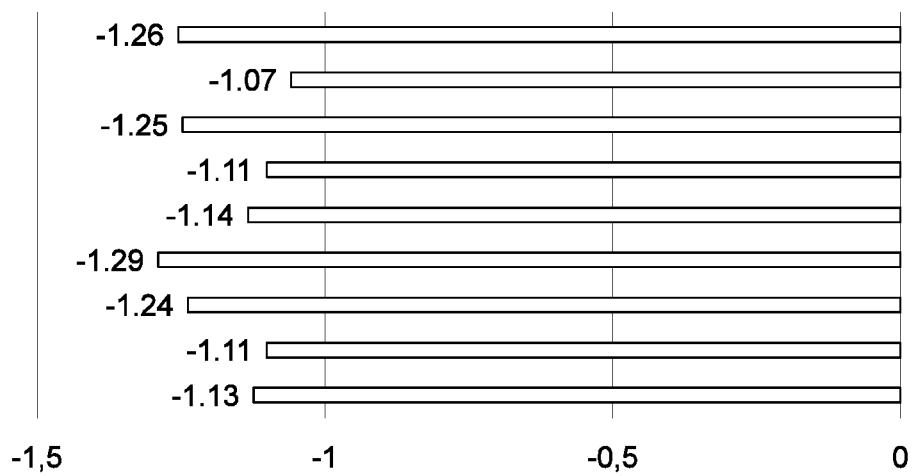
FIG. 16B shows the effect of Ac-SEQ ID NO: 3-NH$_2$ on the gene expression profile of HEMn cells after 24-hour treatment with a peptide concentration of 0.1 mg/mL.

FIG. 16 shows the effect of Ac-SEQ ID NO: 3-$NH_2$ on the gene expression profile of HEMn cells after 11-day (FIG. 16(A)) and 24-hour (FIG. 16(B)) treatment with a peptide concentration of 0.1 mg/mL. Changes in gene expression levels are represented as a positive or negative fold-change with regard to the basal control (untreated cells). For FIG. 16(A), bars from top to bottom in the y-axis refer to: COX-1 (Cyclooxigenase-1), MITF (Melanogenesis associated transcription factor), MC1R (Melanocortin-1 receptor), MLAN-A (Melanoma antigen recognized by T-cells), C-KIT (Protoongogen receptor tyrosine kinase KIT), PMEL17 (Pre-melanosome protein), DCT-TYRP2 (Dopachrome tautomerase), TYRP-1 (Tyrosinase related protein 1) and TYR (Tyrosinase). For FIG. 16(B), bars from top to bottom in the y-axis refer to: BLOC-1 (Biogenesis of lysosome-related organelles complex-1), MITF (Melanogenesis associated transcription factor), MC1R (Melanocortin-1 receptor), MLAN-A (Melanoma antigen recognized by T-cells), C-KIT (Protoongogen receptor tyrosine kinase KIT), PMEL17 (Pre-melanosome protein), DCT-TYRP2 (Dopachrome tautomerase), TYRP-1 (Tyrosinase related protein 1) and TYR (Tyrosinase). The x-axis refers to fold change versus basal control. A negative fold change means that the corresponding gene is downregulated; and a positive fold change means that the corresponding gene is upregulated.

Figure 17:
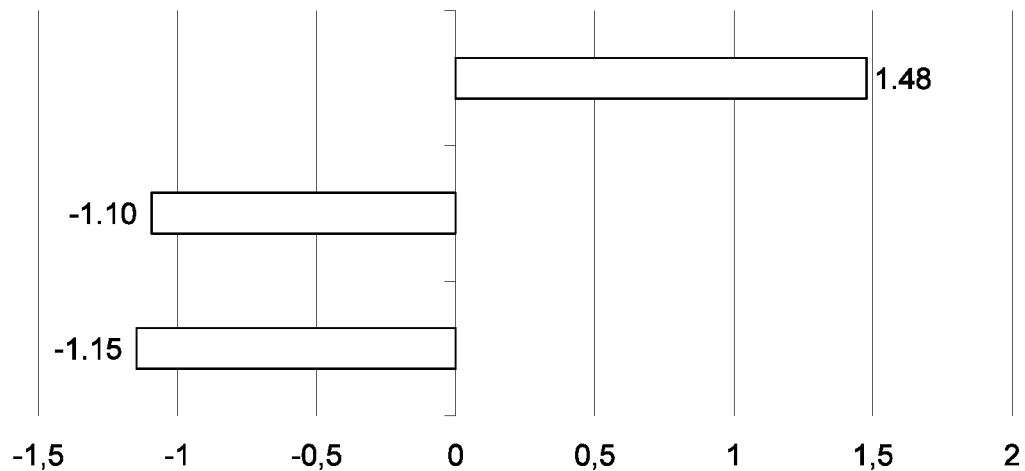
FIG. 17 shows the effect of Ferulic acid-SEQ ID NO: 2-NH$_2$ on the gene expression profile of HEMn cells after 11-day treatment with a peptide concentration of 0.05 mg/mL.

FIG. 17 shows the effect of Ferulic acid-SEQ ID NO: 2-$NH_2$ on the gene expression profile of HEMn cells after 11-day treatment with a peptide concentration of 0.05 mg/mL. Changes in gene expression levels are represented as a positive or negative fold-change with regard to the basal control (untreated cells). Bars from top to bottom in the y-axis refer to: VDR (Vitamin D receptor), PMEL17 (Pre-melanosome protein) and DCT-TYRP2 (Dopachrome tautomerase). The x-axis refers to fold change versus basal control. A negative fold change means that the corresponding gene is downregulated; and a positive fold change means that the corresponding gene is upregulated.

Figure 18:
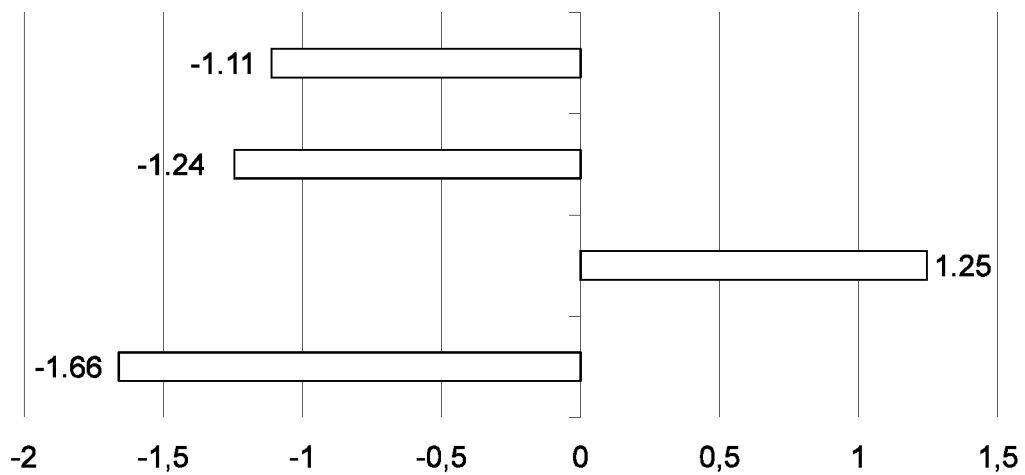
FIG. 18 shows the effect of Ac-SEQ ID NO: 3-NH$_2$ on the gene expression profile of HEKa cells after 24-hour treatment with a peptide concentration of 0.1 mg/mL.

FIG. 18 shows the effect of Ac-SEQ ID NO: 3-$NH_2$ on the gene expression profile of HEKa cells after 24-hour treatment with a peptide concentration of 0.1 mg/mL. Changes in gene expression levels are represented as a positive or negative fold-change with regard to the basal control (untreated cells). Bars from top to bottom in the y-axis refer to: KITLG (KIT ligand), TP53 (Tumor protein p53), DKK1 (Dickkopf-related protein 1) and NGF (Nerve growth factor). The x-axis refers to fold change verus basal control. A negative fold change means that the corresponding gene is downregulated; and a positive fold change means that the corresponding gene is upregulated.

Figure 19:
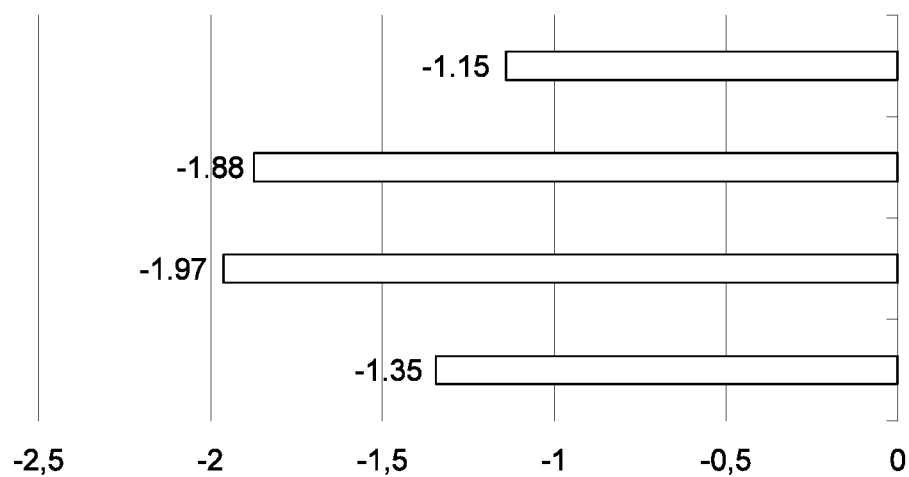
FIG. 19 shows the effect of Ferulic acid-SEQ ID NO: 2-NH$_2$ on the gene expression profile of HEKa cells after 24-hour treatment with a peptide concentration of 0.05 mg/mL.

FIG. 19 shows the effect of Ferulic acid-SEQ ID NO: 2-$NH_2$ on the gene expression profile of HEKa cells after 24-hour treatment with a peptide concentration of 0.05 mg/mL. Changes in gene expression levels are represented as a positive or negative fold-change with regard to the basal control (untreated cells). Bars from top to bottom in the y-axis refer to: KITLG (KIT ligand), POMC (Pro-opiomelanocortin), EDN1 (Endothelin-1) and NGF (Nerve growth factor). The x-axis refers to fold change versus basal control. A negative fold change means that the corresponding gene is downregulated; and a positive fold change means that the corresponding gene is upregulated.

EXAMPLES

Abbreviations

The abbreviations used for amino acids follow the 1983 IUPAC-IUB Joint Commission on Biochemical Nomenclature recommendations outlined in Eur. J. Biochem. (1984) 138:937.

2-ClTrt, 2-chlorotrityl; Ac, acetyl; Arg, arginine; Asp, Aspartic acid; Boc, tert-butyloxycarbonyl; cDNA, complementary DNA; C-terminal, carboxy-terminal; DCM, dichloromethane; DIEA, N,N'-diisopropylethylamine; DIPCDI, N,N'-diisopropylcarbodiimide; DMF, N,N-dimethylformamide; DNA, deoxyribonucleic acid; DPPH, 2,2-diphenyl-1-picrylhydrazyl; equiv, equivalent; ESI-MS, electrospray ionization mass spectrometry; Fmoc, 9-fluorenylmethyloxycarbonyl; Glu, glutamic acid; HDFa, Human Dermal Fibroblasts, adult; HEKa, Human Epidermal Keratinocytes, adult; HEMn, Human Epidermal Melanocytes neonatal; His, histidine; HOBt, 1-hydroxybenzotriazole; HPLC, high performance liquid chromatography; Ile, isoleucine; INCI, International Nomenclature of Cosmetic Ingredients; MBHA, p-methylbenzhydrylamine; Leu, leucine; L Lys, lysine; Me, methyl; MeCN, acetonitrile; MeOH, methanol; N-terminal, amino-terminal; Palm, palmitoyl; Pbf, 2,2,4,6,7-pentamethyldihydrobenzofuran-5-sulfonyl; Phe, phenylalanine; RNA, ribonucleic acid; RT, room temperature; Ser, serine; tBu, tert-butyl; TFA, trifluoroacetic acid; Thr, threonine; TIS, triisopropylsilane; Trp, tryptophan; Trt, triphenylmethyl or trityl; Tyr, tyrosine; Val, valine; Z, benzyloxycarbonyl.

Regarding the chemical synthesis procedures included in the examples, it is noted that all synthetic processes were carried out in polypropylene syringes fitted with porous polyethylene discs or Pyrex® reactors fitted with porous plates. All the reagents and solvents were synthesis quality and were used without any additional treatment. The solvents and soluble reagents were removed by suction. The Fmoc group was removed with piperidine-DMF (2:8, v/v) (at least 1×1 min, 2×10 min, 5 mL/g resin) (Lloyd Williams P. et al., Chemical Approaches to the Synthesis of Peptides and Proteins, C R C, 1997, Boca Raton (Fla., USA)). Washes between stages of deprotection, coupling, and, again, deprotection, were carried out with DMF (3×1 min) and DCM (3×1 min) each time using 10 mL solvent/g resin. Coupling reactions were performed with 3 mL solvent/g resin. The control of the couplings was performed by carrying out the ninhydrin test (Kaiser E. et al., Anal. Biochem., 1970, 34: 595598). All synthetic reactions and washes were carried out at RT.

Example 1. Synthesis and Preparation of the Peptides of the Present Invention Obtaining Fmoc-$X_m$-$AA_1$-$AA_2$-$AA_3$-$AA_4$-$Y_n$—$R_2$-Rink-MBHA-resin, wherein $AA_1$ is -L-Asp- or -L-Glu-; $AA_2$ is -L-Tyr-, -L-Trp- or -L-Phe-; $AA_3$ is -L-Lys- or -L-Arg-; $AA_4$ is -L-Val-, -L-Ile- or -L-Leu-; and n and m, are 0.

Weights were normalized. 4.8 g (2.5 mmol) of the Fmoc-Rink-MBHA resin with a functionalization of 0.52 mmol/g were treated with piperidine-DMF according to the described general protocol in order to remove the Fmoc group. 2.55 g of Fmoc-L-Val-OH, 2.65 g of Fmoc-L-Ile-OH or 2.65 g Fmoc-L-Leu-OH (7.5 mmol; 3 equiv) were incorporated onto the deprotected resin in the presence of DIPCDI (1.17 mL; 7.5 mmol; 3 equiv) and HOBt (1.01 g; 7.5 mmol; 3 equiv) using DMF as a solvent for one hour.

The resin was then washed as described in the general methods and the deprotection treatment of the Fmoc group was repeated to couple the next amino acid. Following the previously described protocols 3.51 g of Fmoc-L-Lys(Boc)-OH or 4.87 g of Fmoc-L-Arg(Pbf)-OH (7.5 mmol; 3 equiv); subsequently 3.45 g of Fmoc-L-Tyr(tBu)-OH, 3.95 g of Fmoc-L-Trp(Boc)-OH or 2.91 g of Fmoc-L-Phe-OH (7.5 mmol; 3 equiv); and subsequently 3.09 g of Fmoc-L-Asp (tBu)-OH or 3.19 g of Fmoc-L-Glu(OtBu)-OH (7.5 mmol; 3 equiv) were coupled, sequentially, each coupling in the presence of 1.01 g of HOBt (7.5 mmol; 3 equiv) and 1.17 mL of DIPCDI (7.5 mmol; 3 equiv). As already noted above, between each amino acid addition step, a deprotection treatment of the Fmoc group was performed.

After the synthesis, the peptide resins were washed with DCM (5 times for 3 minutes each one) and dried under vacuum.

Obtaining Fmoc-$X_m$-$AA_1$-$AA_2$-$AA_3$-$AA_4$-$Y_n$—$R_2$-Rink-MBHA-resin, Wherein X is -L-Leu-; $AA_1$ is -L-His- or -L-Thr-; $AA_2$ is -L-Tyr-, -L-Trp- or -L-Phe-; $AA_3$ is -L-Tyr-, -L-Trp- or -L-Phe-; $AA_4$ is -L-Lys- or -L-Arg- and Y is -L-Ala-; and n and m, are 1.

Weights were normalized. 4.8 g (2.5 mmol) of the Fmoc-Rink-MBHA resin with a functionalization of 0.52 mmol/g were treated with piperidine-DMF according to the described general protocol in order to remove the Fmoc group. 2.34 g of Fmoc-L-Ala-OH (7.5 mmol; 3 equiv) were incorporated onto the deprotected resin in the presence of DIPCDI (1.17 mL; 7.5 mmol; 3 equiv) and HOBt (1.01 g; 7.5 mmol; 3 equiv) using DMF as a solvent for one hour.

The resin was then washed as described in the general methods and the deprotection treatment of the Fmoc group was repeated to couple the next amino acid. Following the previously described protocols 3.51 g of Fmoc-L-Lys(Boc)-OH or 4.87 g of Fmoc-L-Arg(Pbf)-OH (7.5 mmol; 3 equiv); subsequently 3.45 g of Fmoc-L-Tyr(tBu)-OH, 3.95 g of Fmoc-L-Trp(Boc)-OH or 2.91 g of Fmoc-L-Phe-OH (7.5 mmol; 3 equiv); subsequently 3.45 g of Fmoc-L-Tyr(tBu)-OH, 3.95 g of Fmoc-L-Trp(Boc)-OH or 2.91 g of Fmoc-L-Phe-OH (7.5 mmol; 3 equiv); subsequently 4.65 g Fmoc-L-His(Trt)-OH or 2.98 g Fmoc-L-Thr(tBu)-OH (7.5 mmol; 3 equiv); and subsequently 2.65 g of Fmoc-L-Leu-OH (7.5 mmol; 3 equiv) were coupled, sequentially, each coupling in the presence of 1.01 g of HOBt (7.5 mmol; 3 equiv) and 1.17 mL of DIPCDI (7.5 mmol; 3 equiv). As already noted above, between each amino acid addition step, a deprotection treatment of the Fmoc group was performed.

After the synthesis, the peptide resins were washed with DCM (5 times for 3 minutes each one) and dried under vacuum.

Obtaining Fmoc-$X_m$-$AA_1$-$AA_2$-$AA_3$-$AA_4$-$Y_n$—$R_2$—O-2-ClTrt-resin, Wherein $AA_1$ is -L-Asp- or -L-Glu-; $AA_2$ is -L-Tyr-, -L-Trp- or -L-Phe-; $AA_3$ is -L-Lys- or -L-Arg-; $AA_4$ is -L-Val-, -L-Ile- or -L-Leu-; and n and m, are 0.

Weights have been normalized. A mixture of 1.77 g of Fmoc-L-Ile-OH, 1.77 g of Fmoc-L-Leu-OH or 1.70 g of Fmoc-L-Val-OH (5 mmol; 1 equiv) with 0.85 mL of DIEA (5 mmol; 1 equiv) dissolved in approximately 30 mL of DCM were coupled to dry 2-chlorotrityl resin (3.8 g; 5 mmol). They were stirred for 5 min, after which 1.7 mL of DIEA were added (10 mmol; 2 equiv). The mixture was allowed to react for 40 min. The remaining chloride groups were blocked by treatment with MeOH.

The resin was then washed as described in the general methods and the deprotection treatment of the Fmoc group was repeated to couple the next amino acid. Following the previously described protocols 7.02 g of Fmoc-L-Lys(Boc)-OH or 9.74 g of Fmoc-L-Arg(Pbf)-OH (15 mmol; 3 equiv); subsequently 6.90 g of Fmoc-L-Tyr(tBu)-OH, 7.90 g of Fmoc-L-Trp(Boc)-OH or 5.82 g of Fmoc-L-Phe-OH (15 mmol; 3 equiv); and subsequently 6.18 g of Fmoc-L-Asp (tBu)-OH or 6.38 g of Fmoc-L-Glu(OtBu)-OH (15 mmol; 3 equiv) were coupled, sequentially, each coupling in the presence of 2.03 g of HOBt (15 mmol; 3 equiv) and 2.3 mL of DIPCDI (15 mmol; 3 equiv).

After the synthesis, the peptide resins were washed with DCM (5 times for 3 minutes each one) and dried under vacuum.

Using the synthesis procedures mentioned above, with the required selection of amino acids, the following sequences were synthesized:

```
                                    (SEQ ID NO: 1)
   Asp-Tyr-Lys-Val;
   and (SEQ ID NO: 3)
   Leu-His-Trp-Phe-Arg-Ala.
```

In addition, making the appropriate arrangement, also the following sequences were synthesized:

```
                                    (SEQ ID NO: 2)
   His-Trp-Phe-Lys;
   and (SEQ ID NO: 4)
   Thr-Phe-Phe-Lys.
```

Example 2. Removal of Fmoc N-Terminal Protective Group of the Peptides Synthesized in Accordance with Example 1

The N-terminal Fmoc group of the peptidyl resins was deprotected with 20% piperidine in DMF (1×1 min+2×10 min) (Lloyd Williams P. et al. (1997) "Chemical Approaches to the Synthesis of Peptides and Proteins" CRC, Boca Raton (Fla., USA)). The peptidyl resins were washed with DMF (5×1 min), DCM (4×1 min), and dried under vacuum.

Example 3. Process for Introducing the $R_1$ Acetyl Group onto the Peptidyl Resins Obtained in Accordance with Example 2

1 mmol (1 equiv) of the peptidyl resins obtained in accordance with Example 2 was treated with 25 equivalents of acetic anhydride in the presence of 25 equivalents of DIEA using 5 mL of DMF as a solvent. They were left to react for 30 minutes, after which the peptidyl resins were washed with DMF (5×1 min), DCM (4×1 min), and were dried under vacuum.

Example 4. Process for Introducing the $R_1$ Palmitoyl Group onto the Peptidyl Resins Obtained in Example 2

10 equivalents of pre-dissolved palmytic acid in DMF (1 mL) were incorporated onto 1 mmol (1 equiv) of the peptidyl resins obtained in Example 2, in the presence of 10 equivalents of HOBt and 10 equivalents of DIPCDI. They were allowed to react overnight (approximately 15 hours), after which the resins were washed with DMF (5×1 min), DCM (4×1 min), MeOH (5×1 min) and were dried under vacuum.

Example 5. Process for Introducing the $R_1$ Ferulic Acid onto De Peptidyl Resins Obtained in Example 2

10 equivalents of pre-dissolved ferulic acid in DMF (1 mL) were incorporated onto 1 mmol (1 equiv) of the peptidyl resins obtained in Example 2, in the presence of 10 equivalents of HOBt and 10 equivalents of DIPCDI. They were allowed to react for approximately 3-4 hours, after which the resins were washed with DMF (5×1 min), DCM (4×1 min), MeOH (5×1 min) and were dried under vacuum.

Example 6. Cleavage Process from the Polymeric Support of the Peptidyl Resins Obtained in Accordance with Example 2, 3, 4 and 5

Weights were normalized. 200 mg of the dried peptidyl resin obtained in any of Examples 2, 3, 4 or 5 were treated with 5 mL of TFA/TIS/$H_2O$ (90:5:5) for 2 hours at room temperature under stirring. The filtrates were collected and precipitated using 50 mL (8 to 10-fold) of cold diethyl ether. The ethereal solutions were evaporated to dryness at reduced pressure and room temperature, the precipitates are redissolved in 50% MeCN in $H_2O$ and lyophilized.

Example 7. Characterization of the Peptides Synthesized and Prepared in Accordance with Example 6

HPLC analysis of the peptides obtained in accordance with example 5 was carried out with a Shimadzu equipment (Kyoto, Japan) using a reverse-phase column (150×4.6 mm, XBridge Peptide BEH C18, 3.5 µm, Waters, USA) in gradients of MeCN (+0.036% TFA) in $H_2O$ (+0.045% TFA) at a flow rate of 1.25 mL/min and detection was carried out at 220 nm. All peptides showed a purity exceeding 80%. The identity of the peptides obtained was confirmed by ESI-MS in a Water ZQ 4000 detector using MeOH as the mobile phase and a flow rate of 0.2 mL/min.

Example 8. Preparation of a Cosmetic Facial Composition Containing Ac-SEQ ID NO: 1-$NH_2$ A cosmetic facial composition in accordance with table 1 below was prepared. To that end, components from phase A were dissolved in a suitable vessel and the mixture was heated to 70-75° C. In another vessel the components of phase B were mixed together and the mixture was heated to 70-75° C. Next, phase C (TEGOLON 12-10 (INCI: Nylon-12)) was slowly added to phase B, under stirring, until it was completely dissolved. The mixture was heated to 70-75° C. Next the solution of phase A was added to the mixture of phases B and C under turbine stirring to form an emulsion. Next, phase D was slowly added to the mixture, maintaining the stirring until an homogeneous emulsion was obtained. Finally, with the mixture at about 30° C., the commercial formulation containing the compound Ac-SEQ ID NO: 1-$NH_2$ (INCI: Water (Aqua), Glycerin, Caprylyl Glycol, Ac-SEQ ID NO: 1-$NH_2$) was slowly added maintaining stirring.

TABLE 1

Details of the cosmetic facial composition of example 8.

| Phase | Ingredient | % in weight |
|---|---|---|
| A | Water | Quantity required to arrive at 100 |
| A | Disodium EDTA | 0.15 |
| A | Magnesium sulfate | 1.5 |
| A | Glycerin | 2.5 |
| B | Caprylic/Capric triglyceride | 8 |
| B | Isononyl/Isononanoate | 15 |
| B | Polyglyceryl-4 diisostearate/polyhydroxystearate/sebacate | 3 |
| B | Verstatil TBO (INCI: Triethyl citrate, Caprylyl glycol, Benzoic acid): | |
| | Thriethyl citrate | 0.455 |
| | Caprylyl glycol | 0.37 |
| | Benzoic acid | 0.175 |
| B | Synthetic beeswax | 3 |
| C | Nylon-12 | 2 |
| D | BRB SG 516 (INCI: Dimethicone, Dimethicone/Vinyl dimethicone crosspolymer): | |
| | Dimethicone | 1.7 |
| | Dimethicone/Vinyl dimethicone crosspolymer | 0.3 |
| E | Commercial formulation of Ac-SEQ ID NO: 1-$NH_2$ (INCI: Water (Aqua), Glycerin, Caprylyl glycol, Ac-SEQ ID NO: 1-$NH_2$): | |
| | Water (Aqual) | 1.8384 |
| | Glycerin | 0.101 |
| | Caprylyl glycol | 0.0101 |
| | Ac-SEQ ID NO: 1-$NH_2$ | 0.0505 |

Example 9. Trolox Equivalent Antioxidant Capacity (Hereinafter, TEAC)

Peptides Ac-SEQ ID NO: 1-$NH_2$, Ac-SEQ ID NO: 2-$NH_2$, Ac-SEQ ID NO: 3-$NH_2$ and Ferulic acid-SEQ ID NO: 2-$NH_2$ synthesized in accordance with examples 1-6, were used in this example.

TEAC assay was used in this case. Said assay measures the antioxidant capacity of a given substance, as compared to the standard, Trolox, an analogue of Vitamin E.

Antioxidant capacity was measured using the ABTS Decolorization Assay. In this assay, the pre-formed radical monocation of 2,2'-azinobis-(3-ethylbenzothiazoline-6-sulfonic acid) (ABTS*+) was generated by oxidation of ABTS with potassium persulfate and was reduced in the presence of antioxidants (Ac-SEQ ID NO: 1-$NH_2$, Ac-SEQ ID NO: 2-$NH_2$, Ac-SEQ ID NO: 3-$NH_2$ or Ferulic acid-SEQ ID NO: 2-$NH_2$). The ABTS.+ has a blue-green color, with maximum absorptions at 650, 734 and 820 nm. Antioxidants in the sample reduce ABTS.+ suppressing this color production to a degree that is proportional to their concentrations and antioxidant capacity. Quantification of absorbance was conducted at 734 nm using a Polarstar Omega equipment (BMG Labtech).

Results obtained for this experiment appear summarized in FIG. 1. Briefly, for Ac-SEQ ID NO: 1-$NH_2$ the following values of trolox equivalents were obtained: 15 µM at 0.01 mg/mL, 24 µM at 0.05 mg/ml and 94 µM at 0.1 mg/mL; for Ac-SEQ ID NO: 2-$NH_2$ the following values of trolox equivalents were obtained: 22 µM at 0.05 mg/mL, 49 µM at 0.1 mg/mL and 130 µM at 0.5 mg/mL; for Ac-SEQ ID NO: 3-$NH_2$ the following values of trolox equivalents were obtained: 28 µM at 0.01 mg/mL, 59 µM at 0.05 mg/mL and 74 µM at 0.1 mg/mL; and for Ferulic acid-SEQ ID NO: 2-$NH_2$ the following values of trolox equivalents were obtained: 59 µM at 0.01 mg/mL, 112 µM at 0.05 mg/mL1 and 113 µM at 0.1 mg/mL. Results also show that the antioxidant power of Ferulic acid-SEQ ID NO: 2-$NH_2$ is higher than the one of AA-2G at concentrations >0.05 mg/mL and equals MAP values of trolox equivalents at this same concentration. Also, the higher concentration tested of Ac-SEQ ID NO: 2-$NH_2$ showed a higher antioxidant power than AA-2G and MAP.

As derived from the results shown in said figure, the four peptides tested show an important antioxidant power which reaches 94, 130, 74 and 113 µM of Trolox in the higher concentration tested for Ac-SEQ ID NO: 1-$NH_2$, Ac-SEQ ID NO: 2-$NH_2$, Ac-SEQ ID NO: 3-$NH_2$ and Ferulic acid-SEQ ID NO: 2-$NH_2$, respectively. Other antioxidants in the state of the art, like Resveratrol, show an antioxidant capacity of 29 µM of Trolox at 0.02 mg/ml, this is, a markedly lower antioxidant capacity when compared with peptides Ac-SEQ ID NO: 1-$NH_2$, Ac-SEQ ID NO: 2-$NH_2$, Ac-SEQ ID NO: 3-$NH_2$ and Ferulic acid-SEQ ID NO: 2-$NH_2$.

Example 10. Evaluation of Antioxidant Activity

Antioxidant activity of peptide Ferulic acid-SEQ ID NO: 2-$NH_2$ was evaluated in tubo by means of a scavenging assay.

The capacity to scavenge the stable DPPH free radical can be expressed as a measure of antioxidant activity.

During this assay, the purple chromogen (DPPH) radical was reduced by antioxidant/reducing compounds to the corresponding pale-yellow hydrazine. The reduction of the purple chromogen radical by hydrogen-donating antioxidants was monitored by the decrease of optical density at long wavelengths (515-520 nm).

Briefly, different concentrations of Ferulic acid-SEQ ID NO: 2-$NH_2$ (mainly, 0.01 mg/mL, 0.05 mg/mL, 0.1 mg/mL and 0.5 mg/mL) were incubated together with 300 µM DPPH (in MeOH) in triplicate. Ascorbic acid was also included in the assay as positive control for scavenger activity evaluation at 30 µM and 60 µM. After 30 minutes of incubation at room temperature and gentle shaking, the absorbance at 520 nm of each well was determined using the microplate reader Multiskan FC (Thermo Fisher Scientific, MA, USA), being directly proportional to the amount of DPPH left (not-scavenged) in the reaction mixture. Absorbance values were normalized on the basis of the control (non-treated wells) which was stablished as 100%, obtaining the corresponding percentage of activity for each of the treatments.

As shown in FIG. 2, Ferulic acid-SEQ ID NO: 2-$NH_2$ presents a significant antioxidant activity following a dose-response at the higher concentrations tested (0.05 mg/mL, 0.1 mg/mL and 0.5 mg/mL) with a reduction of DPPH of 48.3%, 72.9% and 90.6% respectively. The antioxidant activity of the compound at 0.05 mg/mL and 0.1 mg/mL is comparable to that of ascorbic acid at 30 µM (31.3%) and 60 µM (67.6%), respectively.

Example 11. Thiobarbituric Acid Reactive Substances (Hereinafter, TBARS) Assay

Peptides Ac-SEQ ID NO: 1-$NH_2$ and Ac-SEQ ID NO: 2-$NH_2$, synthesized in accordance with examples 1-3 and 6, were also used in this example.

TBARS are naturally present in biological samples and increase as a result of oxidative stress. This assay measures lipid peroxidation levels through the detection of MDA, a compound that results from the decomposition of polyunsaturated fatty acid lipid peroxides and it is an indicator of oxidative stress in cells and tissues.

Small Unilamellar Vesicles (hereinafter, SUVs) from egg yolk were prepared and incubated with the analysed compounds (peptides Ac-SEQ ID NO: 1-$NH_2$ or Ac-SEQ ID NO: 2-$NH_2$ and the corresponding controls). Then, oxidation of SUVs was induced by the addition of 2,2'-Azobis(2-amidinopropane) dihydrochloride (hereinafter, AAPH), a free radical able to oxidize different molecules. Oxidative reaction was then stopped with Butylated hydroxytoluene (hereinafter, BHT), a lipophilic organic compound with antioxidant properties. Finally, Thiobarbituric Acid (hereinafter, TBA) was added for the detection and quantification of MDA by fluorescence at 530 nm. Fluorescence quantification was performed by Cytation 3 (Biotek).

Results obtained for this assay appear summarized in FIG. 3.

For the two peptides, a statistically significant inhibition of lipid peroxidation was observed in all the concentrations tested.

Example 12. In Vitro Evaluation of the Protective Efficacy Against Oxidative Stress Induced by Hydrogen Peroxide ($H_2O_2$)

Ac-SEQ ID NO: 1-$NH_2$ and Ac-SEQ ID NO: 2-$NH_2$, synthesized in accordance with examples 1-3 and 6, were then tested for their capacity to protect against oxidative stress induced by hydrogen peroxide.

Primary human epidermal keratinocytes were seeded in black 96 well-plates in the corresponding culture medium and, 48 hours later, treated with the different compounds analysed (Ac-SEQ ID NO: 1-$NH_2$ or Ac-SEQ ID NO: 2-$NH_2$) for 3 hours at 37° C. or with ascorbic acid as an antioxidant control. After incubation, cells were loaded with a fluorescence probe for 45 minutes and then $H_2O_2$ was added for 30 minutes.

Finally, fluorescence was determined at Excitation 485 nm/Emission 520 nm.

Results obtained appear summarized in FIG. 4.

As can be directly derived from this figure, both peptides show an inhibition of the oxidative activity exerted by hydrogen peroxide, materialized by a reduction in the reactive oxygen species detected in the sample when treated with any one of the above-mentioned peptides. Noteworthy is the fact that Ac-SEQ ID NO: 1-$NH_2$ has shown increased activity in all concentrations tested when compared with Ac-SEQ ID NO: 2-$NH_2$.

Example 13. In Vitro Evaluation of the Protective Efficacy Against Glycation Induced by Heavy Metals (Advanced Glycation End Products Modulation)

Peptide Ac-SEQ ID NO: 1-$NH_2$, synthesized in accordance with examples 1-3 and 6, was also tested for its capacity to protect against glycation induced by heavy metals.

Primary human epidermal keratinocytes were seeded in 96-well plates in standard culture medium and, 24 hours later, subjected to a simultaneous treatment with heavy metals (containing a mixture of Fe, Pb and Cr) and peptide Ac-SEQ ID NO: 1-NH$_2$ for 48 hours. Levels of Advance Glycation End (AGE) products were measured by means of a competitive ELISA assay with absorbance at 450 nm.

The results obtained in this assay are summarized in FIG. 5.

As can be seen in FIG. 5, all concentrations tested of the peptide Ac-SEQ ID NO: 1-NH$_2$ produced a statistically significant decrease in the quantity of advanced glycation end-products, reducing it to levels near those observed in the basal state (quantity or level in control samples not treated with heavy metals or in the treated samples prior to the application of the treatment with the heavy metals).

Example 14. In Vitro Evaluation of the Protective Efficacy Against DNA Oxidation and Lipoxidation Induced by Synthetic Smoke (8-Hydroxy-2'-Deoxyguanosine(8-OHdG) Modulation)

The antioxidant activity of peptide Ac-SEQ ID NO: 1-NH$_2$, synthesized in accordance with examples 1-3 and 6, was also analysed by treating the samples with synthetic smoke.

Primary human epidermal keratinocytes were seeded in 96-well plates in standard culture medium and, 24 hours later, subjected to a simultaneous treatment with synthetic smoke containing selected compounds from the particle phase (for example, cadmium and nicotine) and vapour phase (for example, formaldehyde (hereinafter, FA) and ethyl carbamate) of tobacco smoke and the analysed compound (Ac-SEQ ID NO: 1-NH$_2$) for 48 h.

After treatment, cells were lysed and DNA oxidation on cell homogenates was analysed measuring levels of 8-OHdG by means of a competitive ELISA assay with absorbance at 450 nm.

In addition, after treatment, lipoxidation was analysed by means of the levels of intracellular MDA, which were measured by the reaction between MDA and N-methyl-2-phenylindole (hereinafter, NMPI) rendering a stable blue chromopore with an absorption peak at 586 nm.

The outcome of this assays is shown in FIGS. 6 and 7.

From both figures, it can be derived that Ac-SEQ ID NO: 1-NH$_2$ is able to protect cells against DNA oxidation and lipoxidation. In fact, for these two parameters, the behavior was similar: the lower tested concentration showed a slight decrease (non-statistically significant) for said parameters while the other two tested concentrations showed a higher, statistically significant, effect which, in the case of protection of DNA oxidation leads to an almost complete inhibition of the effects of synthetic smoke as the levels of DNA oxidation observed in the samples treated with 0.1 mg/ml approaches to that observed in the basal state (this is, in the non-treated control sample).

Example 15. Modulation of the Expression of Antioxidant Genes

Modulation of gene expression by Ac-SEQ ID NO: 1-NH$_2$ was evaluated in vitro on HEKa cells.

Briefly, HEKa cells were seeded in duplicate in 6-well plates at a density of 4×10$^5$ cells/well and maintained at standard culture conditions (37° C., 95% humidity, 5% CO$_2$) for 24 hours. Then, cells were treated with non-cytotoxic concentrations of Ac-SEQ ID NO: 1-NH$_2$ (0.05 mg/mL) for an additional 24 hours.

Untreated cells were used as basal control. Cells were then lysed for RNA extraction with a RNA purification commercial kit following manufacturer instructions (RNeasy mini kit; Qiagen; Netherlands). RNA was then quantified by nanodrop, adjusted in concentration and processed for retrotranscription to cDNA using a commercially available kit (High-Capacity cDNA Reverse Transcription kit; Thermofisher Scientific, USA). Resulting cDNA was used to perform a RTqPCR (Real Time Quantitative Polymerase Chain Reaction) using Taqman technology and a panel of probes designed to target specific genes related to melanogenesis and HEMn-HEKa and HEMn-HDFa communication.

The results of this example appear summarized in FIG. 8.

Said figure shows that treatment with 0.05 mg/mL of As-SEQ ID NO: 1-NH$_2$ induces the upregulation of key antioxidant genes with the following fold change: CYP2R1 (1.44), NFE2L2 (1.23), HMOX1 (1.48), GSTP1 (1.13), GSS (1.10), GPX1 (1.22) and TRX (1.34). Therefore, peptide Ac-SEQ ID NO: 1-NH$_2$ not only shows a high intrinsic antioxidant activity, as seen in Example 9, but, also, through the increase in the expression of key antioxidant genes such as NFE2L2 and HMOX-1, it is able to protect several biological structures, such as proteins, lipids and DNA against multiple stressors, as heavy metals and tobacco smoke.

Example 16. Antioxidant and Anti-Pollutant Capacity of Ac-SEQ ID NO: 1-NH$_2$ on Human Skin Explants The protection efficacy of peptide Ac-SEQ ID NO: 1-NH$_2$ against pollution aggression on human living explants was assessed by observation of the general morphology, immunostaining of AhR and HO-1 (both are known markers of oxidative stress as they have been related to anti-oxidative response) (Esser C., Bargen I., Weighardt H., Haarmann-Stemmann T., Krutmann J., *Functions of the aryl hydrocarbon receptor in the skin*, Semin Immunopathol (2013) 35:677-691; Kohen R., Nyska A., *Oxidation of Biological Systems: Oxidative Stress Phenomena, Antioxidants, Redox Reactions, and Methods for Their Quantification*, Toxicologic Pathology (2002) vol 30, no 6, 620-650).

Briefly, human skin explants from a 49-year-old Caucasian woman were put in culture under controlled conditions. 21 skin explants of an average diameter of 11 mm (±1 mm) were prepared and kept in survival in BEM culture medium at 37° C. in a humid, 5% CO$_2$ atmosphere. The explants were distributed in 5 batches: explant control (Time=0), control batch, explants treated with the above-mentioned peptide, explants treated with pollutant and explants treated with pollutant and with the above-mentioned peptide. A composition containing Ac-SEQ ID NO: 1-NH$_2$ in accordance with Example 8 was prepared and it was topically applied on days 0, 1, 3 and 4. Untreated explants were used as controls and did not received any treatment. For each condition, half of the explants were afterwards exposed to a pollutant mixture containing Benzene, Xylene, Toluene, heavy metals and hydrocarbons. Explant exposure was performed 3 hours after the treatment with Ac-SEQ ID NO: 1-NH$_2$ using a Pollubox® system (BIO-EC, Longjumeau, France) and lasted for 1.5 hours. Samples were processed for histology at day 0 and day 5. The observation of the general morphology was performed after staining of paraffinized sections according to Masson's trichrome, Goldner variant. AhR immunostaining was performed on paraffin sections with a monoclonal anti-AhR antibody (Thermoscientific, ref. MA1-514, clone RPT1, MA, USA) and HO-1 with a monoclonal anti-HO-1 antibody (Novus biologicals, ref. NBP1-97507, CO, USA). Finally, image analyses and quantification were performed using Cell^D software (Olympus, Tokyo, Japan).

Results of this experiment appear summarized in FIG. 9, where the antioxidant efficacy (amount of AhR and HO-1) of peptide Ac-SEQ ID NO: 1-NH$_2$ on human skin explants, treated with said peptide in a formulation, can be observed.

As it can be seen in FIG. 9(C), it was confirmed the antioxidant effect of Ac-SEQ ID NO: 1-NH$_2$ as it is directly derivable from its efficacy in increasing the expression on HO-1 for the prevention of oxidative damage and oxidative stress. After treatment of skin explants with the peptide in a final formulation (without exposure to pollutants), the levels of HO-1 significantly increased by 69% (FIG. 9C) when compared to untreated and unexposed explants.

As observed in FIGS. 9(A) and 9(B), Ac-SEQ ID NO: 1-NH$_2$ showed an anti-pollution and anti-oxidant activity by reducing the anti-oxidant response required by the explants, which can be readily ascertained by the observed decrease in AhR (16%) and HO-1 (23%), respectively, compared to the levels expressed with pollutants and without treatment with the peptide. This is so because, the pretreatment with the peptide of the present invention (in this case Ac-SEQ ID NO: 1-NH$_2$) would already induce an anti-oxidant response preparing the explants for any future or subsequent oxidative insult and, hence, when said oxidative insult arrives or is performed (in the present case, exposure of the cells to pollutants), the cells require less anti-oxidative response and the anti-oxidative machinery already prepared is used or consumed against said oxidative insult (see, for example, FIG. 9(C)).

Therefore, the peptides of the present invention, are effective in the prevention of oxidative stress and its consequences.

It is of special interest the enzyme HO-1 or HMOX-1, detected both at the genetic level and in the skin explants, which is known to be an enzyme activated via NFE2L2 (also detected in the smart data gene panel), known as the antioxidant switch, which is itself a transcription factor that binds to antioxidant-responsive elements (AREs), enhancer DNA sequences that initiate the transcription of a battery of genes encoding potent antioxidant enzymes (Nguyen, T., Nioi, P., and Pickett, C. B., *The Nrf2-Antioxidant Response Element Signaling Pathway and Its Activation by Oxidative Stress*, J. Biol. Chem., 284 (2009) 13291-13295). Ac-SEQ ID NO: 1-NH$_2$ also acts as a modulator of the increased expression of AhR induced after pollutants exposure, as observed on human skin explants, therefore, preventing the oxidative damage associated with AhR activation and the subsequent hyperpigmentation, also observed in vitro through inhibition of melanin synthesis.

The results shown in Examples 9 to 16 demonstrate that the peptides of the present invention, as exemplified by Ac-SEQ ID NO: 1-NH$_2$, Ac-SEQ ID NO: 2-NH$_2$, Ac-SEQ ID NO: 3-NH$_2$ and Ferulic acid-SEQ ID NO: 2-NH$_2$, have not only a potent antioxidant activity but also that said activity is wide-spectrum. This is, in all the oxidative conditions tested and for all the parameters tested the peptides have shown a significant and important activity.

Hence, these experimental results demonstrate the feasibility of these peptides to be used in cosmetic compositions or methods to prevent, reduce and/or remove skin imperfections related with oxidation and oxidative stress as, for example, skin complexion, pigmentation alterations or other age related or environment related skin imperfections. This is so, because, the analysed activities are directly related with oxidative stress (Gkogkolou P, Böhm M, *Advanced glycation end products Key players in skin aging?*, Dermatoendocrinol., 2012 Jul. 1; 4(3): 259-270; Sciskalska M, Zalewska M, Grzelak A, and Milnerowicz H, *The Influence of the Occupational Exposure to Heavy Metals and Tobacco Smoke on the Selected Oxidative Stress Markers in Smelters*, Biol Trace Elem Res., 2014; 159(1-3): 59-68; Tchounwou P B, Yedjou C G, Patlolla A K, and Sutton D J, *Heavy Metals Toxicity and the Environment*, EXS., 2012; 101: 133-164; Aflanie I, *Effect of Heavy Metal on Malondialdehyde and Advanced Oxidation Protein Products Concentration: A Focus on Arsenic, Cadmium, and Mercury*, Journal of Medical and Bioengineering Vol. 4, No. 4, August 2015; van der Vaart H, Postma D S, Timens W, ten Hacken N H, *Acute effects of cigarette smoke on inflammation and oxidative stress: a review*, Thorax., 2004 August; 59(8):713-21; and Danielsen PH1, Møller P, Jensen K A, Sharma A K, Wallin H, Bossi R, Autrup H, Mølhave L, Ravanat J L, Briedé J J, de Kok T M, Loft S, *Oxidative stress, DNA damage, and inflammation induced by ambient air and wood smoke particulate matter in human A549 and THP-1 cell lines*, Chem Res Toxicol., 2011 Feb. 18; 24(2):168-84).

Example 17. Brightening Activity Studies

Peptides Ac-SEQ ID NO: 1-NH$_2$, Ac-SEQ ID NO: 2-NH$_2$, Ac-SEQ ID NO: 3-NH$_2$ and Ferulic acid-SEQ ID NO: 2-NH$_2$ synthesized in accordance with examples 1-6, were used in this example.

Primary human epidermal melanocytes were incubated in 6-well plates for 4 days and then treated with the compounds to be analysed (Ac-SEQ ID NO: 1-NH$_2$, Ac-SEQ ID NO: 2-NH$_2$, Ac-SEQ ID NO: 3-NH$_2$ or Ferulic acid-SEQ ID NO: 2-NH$_2$) for 7 days. After treatment, cells were homogenized an intracellular melanin content was quantified by absorbance at 450 nm by Multiskan FC (Thermo Fisher Scientific, MA, USA).

Results obtained in this example appear summarized in FIGS. 10 to 13.

As can be readily derivable from the results shown in FIGS. 10 and 11, both peptide Ac-SEQ ID NO: 1-NH$_2$ and Ac-SEQ ID NO: 2-NH$_2$ in all the concentrations tested have a significantly higher brightening or whitening activity when compared with kojic acid, a reference compound for this activity. This increased activity ranges from two to more than four times the activity seen for the two concentrations of kojic acid. In addition, it is also noteworthy that even at lower concentrations, the peptides of the present invention exert a markedly increased brightening activity with regards to kojic acid (see lower concentration used for Ac-SEQ ID NO: 1-NH$_2$ −17.7 µM—and Ac-SEQ ID NO:2-NH$_2$ −15.2 µM—when compared with 50 µM of kojic acid).

As observed in FIGS. 12 and 13, peptides Ac-SEQ ID NO: 3-NH$_2$ and Ferulic acid-SEQ ID NO: 2-NH$_2$ also show a significant decrease in melanin content, which is higher than the positive reference control (treatment with kojic acid) in case of Ac-SEQ ID NO: 3-NH$_2$ (up to 49.3% at 0.1 mg/mL) but comparable in the case of Ferulic acid-SEQ ID NO: 2-NH$_2$ (36% decrease at 0.05 mg/mL).

Example 18. Evaluation of Tyrosinase Activity

The potential of peptides Ac-SEQ ID NO: 3-NH$_2$ and Ferulic acid-SEQ ID NO: 2-NH$_2$ to inhibit tyrosinase activity was evaluated in tubo.

Briefly, different concentrations of Ac-SEQ ID NO: 3-$NH_2$ and Ferulic acid-SEQ ID NO: 2-$NH_2$ (0.1, 0.5 and 1 mg/mL) and the positive control kojic acid (400 and 800 µM) were incubated with recombinant mushroom tyrosinase for 30 minutes before the addition of L-DOPA (L-3,4 dihydroxyfenylalanine, 2.5 mg/mL in PBS). After 2 hours' reaction at room temperature, the absorbance at 450 nm of each well was determined using the microplate reader Multiskan FC (Thermo Fisher Scientific, MA, USA), which is directly proportional to the amount of dopachrome in the reaction mixture.

Absorbance values were normalized with regard to non-treated wells (control) which were stablished as 100%, obtaining, hence, the percentage of activity for each condition tested.

Results appear summarized in FIGS. 14 and 15.

Results in FIG. 14 show a significant decrease in tyrosinase activity after treatment with 0.5 mg/mL (30.6%) and 1 mg/mL (58.1%) of Ac-SEQ ID NO: 3-$NH_2$, reaching percentages close to those of kojic acid at 800 µM. Similarly, Ferulic acid-SEQ ID NO: 2-$NH_2$ induced a dose-response reduction in tyrosinase activity, with a decrease of 12%, 46.5% and 71% at 0.05 mg/mL, 0.1 mg/mL and 0.5 mg/mL, respectively (see FIG. 15).

Example 19. Modulation in Gene Expression of Melanogenic Pathways

Modulation of gene expression by Ac-SEQ ID NO: 3-$NH_2$ and Ferulic acid-SEQ ID NO: 2-$NH_2$ peptides was evaluated in vitro on two different cell types (HEMn and HEKa).

Briefly, HEKa cells were seeded in duplicate in 6-well plates at a density of $4 \times 10^5$ cells/well and maintained at standard culture conditions (37° C., 95% humidity, 5% $CO_2$) for 24 hours. Then, cells were treated with non-cytotoxic concentrations of Ac-SEQ ID NO: 3-$NH_2$ (0.1 mg/mL) or Ferulic acid-SEQ ID NO: 2-$NH_2$ (0.05 mg/mL) for an additional 24 hours.

In the case of HEMn cells, cells were left in culture for 12 days (from day 0 to day 11, 11-day treatment) at standard culture conditions (37° C., 95% humidity, 5% $CO_2$) and treated with non-cytotoxic concentrations of Ac-SEQ ID NO: 3-$NH_2$ (0.1 mg/mL) or Ferulic acid-SEQ ID NO: 2-$NH_2$ (0.05 mg/mL) from day 4 to day 11.

In addition, HEMn cells were left in culture for 24 h at standard culture conditions (37° C., 95% humidity, 5% $CO_2$) and treated with a non-cytotoxic concentration of Ac-SEQ ID NO: 3-$NH_2$ (0.1 mg/mL) for additional 24 h.

Untreated cells were used as basal control. Cells were then lysed for RNA extraction with a RNA purification commercial kit following manufacturer instructions (RNeasy mini kit, Qiagen, Netherlands). RNA was then quantified by nanodrop, adjusted in concentration and processed for retrotranscription to cDNA using a commercially available kit (High-Capacity cDNA Reverse Transcription kit—Thermofisher Scientific, USA). Resulting cDNA was used to perform a RTqPCR (Real Time Quantitative Polymerase Chain Reaction) using Taqman technology and a panel of probes designed to target specific genes related to melanogenesis and HEMn-HEKa and HEMn-HDFa communication.

The results of this example appear summarized in FIGS. 16 to 19 (FIGS. 16 and 17 for modulation in HEMn and, FIGS. 18 and 19 for modulation in HEKa).

Said FIG. 16 shows that treatment with 0.1 mg/mL of Ac-SEQ ID NO: 3-$NH_2$ (FIG. 16) induces a downregulation of several genes involved in the melanogenic pathway at 11-day treatment, with the following fold change: COX-1 (−1.51), MITF (−1.48), MC1R (−1.28), MLAN-A (−1.88), C-KIT (−1.78), PMEL17 (−2.30), DCT-TYRP2 (−1.40), TYRP-1 (−1.64) and TYR (−1.66). When treatment was performed at 24 h, this tendency to downregulate gene expression was also observed.

In the case of Ferulic acid-SEQ ID NO: 2-$NH_2$ (FIG. 17), an upregulation of VDR gene (fold change of 1.48) and a slight tendency to downregulate PMEL17 and DCT-TYRP2 expression was observed.

FIGS. 18 and 19 show the regulation of genes involved in HEMn-HEKa communication and release of melanogenic factors. A 24-hour treatment of HEKa cells with 0.1 mg/mL of Ac-SEQ ID NO: 3-$NH_2$ induced the downregulation of KITLG, TP53 and NGF and the upregulation of DKK-1 (FIG. 18). A lower concentration of Ferulic acid-SEQ ID NO: 2-$NH_2$ (0.05 mg/mL) induced de downregulation of KITLG, POMC, EDN1 and NGF (FIG. 19).

The above results demonstrate the feasibility of the peptides of the present invention, as exemplified by Ac-SEQ ID NO: 1-$NH_2$, Ac-SEQ ID NO: 2-$NH_2$, Ac-SEQ ID NO: 3-$NH_2$ and Ferulic acid-SEQ ID NO: 2-$NH_2$, to be used in cosmetic compositions or methods to lighten or brighten skin.

The invention claimed is:

1. A peptide having formula (I), wherein the peptide of formula (I) is:

$R_1$-Asp-Tyr-Lys-Val-$R_2$; ($R_1$-SEQ ID NO: 1-$R_2$)

$R_1$-His-Trp-Phe-Lys-$R_2$; ($R_1$-SEQ ID NO: 2-$R_2$)

$R_1$-Leu-His-Trp-Phe-Arg-Ala-$R_2$; ($R_1$-SEQ ID NO: 3-$R_2$)
or $R_1$-Thr-Phe-Phe-Lys-$R_2$. ($R_1$-SEQ ID NO: 4-$R_2$)

wherein $R_1$ is an acetyl moiety or ferulic acid moiety and $R_2$ is $NH_2$.

2. The peptide according to claim 1, wherein the peptide of formula (I) is:

Ac-Asp-Tyr-Lys-Val-$NH_2$; (Ac-SEQ ID NO: 1-$NH_2$)

Ac-His-Trp-Phe-Lys-$NH_2$; (Ac-SEQ ID NO: 2-$NH_2$)

Ferulic acid-His-Trp-Phe-Lys-$NH_2$; (Ferulic acid-SEQ ID NO: 2-$NH_2$)
or

Ac-Leu-His-Trp-Phe-Arg-Ala-$NH_2$. (Ac-SEQ ID NO: 3-$NH_2$)

3. The peptide according to claim 1, wherein the peptide of formula (I) is:

Ac-Asp-Tyr-Lys-Val-$NH_2$; (Ac-SEQ ID NO: 1-$NH_2$)
or

Ac-His-Trp-Phe-Lys-$NH_2$. (Ac-SEQ ID NO: 2-$NH_2$)

4. A cosmetic composition comprising the peptide according to claim 1.

5. The cosmetic composition according to claim 4, comprising 0.1%-0.0001% (m/v) of the peptide.

6. A method for reducing or removing oxidative stress in the skin of a subject in need thereof comprising applying the cosmetic composition according to claim 4 to the skin of the subject.

7. A method for brightening the skin of a subject in need thereof comprising applying the cosmetic composition according to claim 4 to the skin of the subject.

8. A method for reducing or removing oxidative stress in the skin of a subject in need thereof, comprising applying the peptide of claim 1 to the skin of the subject.

9. A method for brightening the skin of a subject in need thereof comprising applying the peptide of claim 1 to the skin of the subject.

* * * * *

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Artificially synthesized peptide

<400> SEQUENCE: 1

Asp Tyr Lys Val
1

<210> SEQ ID NO 2
<211> LENGTH: 4
<212> TYPE: PRT
```

```
<213> ORGANISM: Artificial Sequence
<220> FEATURE:
<223> OTHER INFORMATION: Atificially synthesized peptide

<400> SEQUENCE: 2

His Trp Phe Lys
1

<210> SEQ ID NO 3
<211> LENGTH: 6
<212> TYPE: PRT
<213> ORGANISM: Artificial Sequence
<220> FEATURE:
<223> OTHER INFORMATION: Artificially synthesized peptide

<400> SEQUENCE: 3

Leu His Trp Phe Arg Ala
1               5

<210> SEQ ID NO 4
<211> LENGTH: 4
<212> TYPE: PRT
<213> ORGANISM: Artificial Sequence
<220> FEATURE:
<223> OTHER INFORMATION: Artificially synthesized peptide

<400> SEQUENCE: 4

Thr Phe Phe Lys
1
```